United States Patent
Henkel et al.

(10) Patent No.: US 10,638,757 B2
(45) Date of Patent: May 5, 2020

(54) FORMULATION SYSTEMS FOR ANTIMICROBIAL GLYCOLIPIDS

(71) Applicant: IMD Natural Solutions GmbH, Dortmund (DE)

(72) Inventors: Thomas Henkel, Dortmund (DE); Jens Bitzer, Dortmund (DE)

(73) Assignee: IMD Natural Solutions GmbH, Dortmund (DE)

( * ) Notice: Subject to any disclaimer, the term of this patent is extended or adjusted under 35 U.S.C. 154(b) by 0 days.

(21) Appl. No.: 16/088,265

(22) PCT Filed: Apr. 11, 2017

(86) PCT No.: PCT/EP2017/058702
§ 371 (c)(1),
(2) Date: Sep. 25, 2018

(87) PCT Pub. No.: WO2017/178497
PCT Pub. Date: Oct. 19, 2017

(65) Prior Publication Data
US 2019/0082689 A1    Mar. 21, 2019

(30) Foreign Application Priority Data

Apr. 13, 2016  (EP) .................................. 16165029

(51) Int. Cl.
| | |
|---|---|
| C07H 15/04 | (2006.01) |
| A61K 31/7032 | (2006.01) |
| A01N 43/14 | (2006.01) |
| A23L 2/44 | (2006.01) |
| A23L 3/3517 | (2006.01) |
| A23L 33/00 | (2016.01) |
| A01N 63/10 | (2020.01) |
| A23L 33/10 | (2016.01) |
| A01N 25/22 | (2006.01) |
| C07H 15/06 | (2006.01) |

(52) U.S. Cl.
CPC ............ *A01N 43/14* (2013.01); *A01N 25/22* (2013.01); *A01N 63/10* (2020.01); *A23L 2/44* (2013.01); *A23L 3/3517* (2013.01); *A23L 33/00* (2016.08); *A23L 33/10* (2016.08); *A61K 31/7032* (2013.01); *C07H 15/04* (2013.01); *C07H 15/06* (2013.01); *A23V 2002/00* (2013.01)

(58) Field of Classification Search
None
See application file for complete search history.

(56) References Cited

U.S. PATENT DOCUMENTS

| | | |
|---|---|---|
| 2014/0017844 A1 | 1/2014 | Anderson et al. |
| 2018/0297747 A1 | 10/2018 | Lee |

FOREIGN PATENT DOCUMENTS

JP      2006176438 A2      7/2006

OTHER PUBLICATIONS

Nishida, Fumiko et al., "Structural elucidation of glycosidic antibiotics produced by Basidiomycetes", Jan. 1, 1987, retrieved from Canada database, XP002665786, six pages.
Nishida, Fumiko, "Glykenin", Jan. 1, 1996, retrieved from Canada database, XP002665785, 18 pages.
Fumiko, Nishida et al., "Structure Elucidation of Glycosidic Antibiotics, Glykenins from Basidiomycetes . . . ", Chem Pharm Bull, vol. 38, No. 9, Jan. 1, 1990, XP055014664, pages pp. 2381-2389.
Nishida, F., et al., "Structure Elucidation of Glycosidic Antibiotics Glykenins from *Basidiomycetes* sp, III. Structure of Glykenin IV", The Journal of Antibiotics, Nature Publishing Group, GB, vol. 44, No. 5, Jan. 1, 1991, XP009154880, pp. 541-545.
Fumiko, Nishida et al., "Structures of Deacetyl Glykenins-A, B. and C, Glycosidic Antibiotics from *Basidiomycetes* sp.", Tetrahedron Letters, vol. 29, No. 41, Jan. 1, 1988, XP0055014672, pp. 5287-5289.
International Search Report from International Publication No. PCT/EP2017/058702, dated May 30, 2017, two pages.

*Primary Examiner* — Eric Olson
(74) *Attorney, Agent, or Firm* — Nicanor Kohncke

(57) ABSTRACT

The invention relates to a composition comprising one or more antimicrobial glycolipids and one or more formulation stabilizers. The invention also relates to methods of preparing the compositions and their application in water containing food, beverage, cosmetic, home care and medical products.

16 Claims, No Drawings

FORMULATION SYSTEMS FOR ANTIMICROBIAL GLYCOLIPIDS

The invention relates to a composition comprising one or more antimicrobial glycolipids and one or more formulation stabilizers which preferably comprise me or more polysorbates and/or one or more cyclodextrins, preferably alpha-cyclodextrin. The invention also relates to methods of preparing the compositions and their application in water containing food, beverage, cosmetic, home care and medical products.

Bacteria and fungi cause food and beverage products, cosmetic and home care products as well as other products so go bad, thereby reducing the shelf life or useful life of such products or goods. Food and cosmetic products therefore require good protection against microbiological contamination; and for certain household and medicinal products an antimicrobial efficacy is desired. Numerous efforts have been made to reduce the deleterious effects of microbial contaminants in food and beverage, cosmetics, home care and medicinal products.

Food preservatives such as salt, sugar and vinegar have been used for generations and while relatively safe to use, their preservative effect is limited in both duration of effect and the types of food and beverages for which they can be used. In addition, at higher levels, preservatives such as salt and vinegar can affect the taste and health impact of the product.

Commonly used preservatives for cosmetics and partially also in foods include antimicrobial agents such as quaternary ammonium compounds, alcohols, chlorinated phenols, parabens and paraben salts, imidazolidinyl urea, phenoxyethanol, p-hydroxybenzoate, small carboxylic acids like benzoic acid, sorbic acid, salicylic acid, lactic acid, formic acid, propionic acid or corresponding salts. Formaldehyde-releasers and isothiazoliones may also be used.

However, these materials often may not be tolerated or, e.g. in the case of formaldehyde, may even be toxic and even carcinogenic, or they may cause allergies or food intolerance. Further, some microorganisms, in particular among the spoilage yeasts, have adopted resistance or tolerance towards one or more of the commonly used preservatives.

Another preservative used in food and especially beverages is sulfuric acid, while in meat products, e.g. sausages, preserved meat and meat, stabilizers which decrease water activity such as potassium and/or sodium nitrites and nitrates are often added. Also smoke is often used for preserving meat products, with the undesirable side effect of formation of polycyclic aromatic hydrocarbons which have carcinogenic properties.

In summary, many preservatives and preservation methods have undesirable side effects, such as toxicity, allergenicity, carcinogenicity, occasionally formation of resistance, and/or often are not accepted by the consumers in a time where natural preservation is preferred over preservation with synthetic or other products having a negative health image.

Accordingly, a great need exists for effective, relatively inexpensive, non-toxic, naturally derived preservative compositions that avoid disadvantages as mentioned and are capable of reducing microbial contamination and concomitant spoilage in a wide range of perishable food, beverages, cosmetics, other consumer goods as well as medical products, but without appreciably altering the taste, colour, odour, or function of the product.

Glycolipids derived from the cultivation of fungal species of the Dacrymycetaceae family demonstrate an antimicrobial efficacy suitable to act as preservative and antimicrobial agent. WO 2012/167920 A1 describes glycolipids found and isolated from strains of Dacryopinax spathularia and other fungal strains belonging to the Dacrymycetaceae family. These glycolipids exhibit strong inhibition activity against microorganisms which are responsible for spoiling or deterioration of orally consumable products (such as food products and beverages) or cosmetic compositions.

These glycolipids are very well water soluble at concentrations even higher than 10% resulting in clear solutions. Such solutions are stable and can be stored for months at room temperature without changes in their appearance, physical-chemical properties or antimicrobial activity.

However, in particular at higher concentrations in water based products, such as beverages, an initially clear solution of the glycolipids turns slightly turbid or cloudy within 1-2 weeks. In some emulsified cloudy beverages, the emulsion shows signs of disturbance within 1-2 weeks and precipitates as well as separated liquid phases can partially be observed.

Thus, the formulations of the glycolipids in water are not always stable over time at all concentrations and compatibility of the antimicrobial glycolipids with emulsions is not always given. Consequently, there is a demand for improved formulation systems allowing broad utilization of antimicrobial glycolipids in water based products without having compatibility issues such as described above.

It is an object of the invention to provide formulation systems which exhibit antimicrobial properties such that they can be utilized for preserving orally consumable water based products, e.g. beverages, and which have advantages compared to the prior art.

This object has been achieved by the subject-matter of the patent claims.

A first aspect of the invention relates to a composition comprising
(i) a glycolipid component comprising at least one antimicrobial glycolipid according to general formula (I)

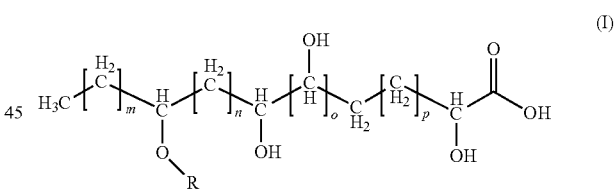

wherein
m is 3 to 5; preferably 3 or 5;
n is 2 to 5; preferably 3;
o is 0 or 1; and
p is 3 to 17; preferably p is 5 to 15; more preferably 11 or 13;
with the proviso that the sum m+n+o+p is not less than 14; and
R is a carbohydrate moiety bound via one of its carbon atoms to the binding oxygen;
or an ester thereof, in open chain form and/or in form of a lactone; and/or a physiologically acceptable salt thereof; and
(ii) a formulation component comprising at least one formulation stabiliser, preferably one or more polysorbates and/or am or more cyclodextrins, preferably alpha-cyclodextrin;
wherein the relative weight ratio of said formulation component to said glycolipid component is within the range of from 100:1 to 1:2, based on the total weight of all antimicrobial glycolipids according to general formula (I) in the composition and based on the total weight of all formulation stabilizers in the composition.

The invention relates to the interaction between antimicrobial glycolipids with formulation components which preferably comprise one or more polysorbates and/or one or more cyclodextrins preferably alpha-cyclodextrin, as formulation stabilizers. As a result of this interaction, formulations (e.g. solutions or emulsions) of the antimicrobial glycolipid in water based applications are surprisingly stabilized and the compatibility for a broad use in applications such as foods, beverages, cosmetics, home care and medicinal products, containing various other ingredients, is improved, while the microbiological inhibitory activity is retained.

As to better understand such observations and potential interactions with formulation stabilizers, a mixture of antimicrobial glycolipids was added to water as well as selected clear and cloudy beverages in which several formulation stabilizers had been pre-dissolved at different concentrations. Such selected beverages had been shown previously a lack in compatibility, i.e. demonstrated increased turbidity or disturbances of their emulsions within 1-2 weeks after treatment with a mixture of antimicrobial glycolipids. However, most of the formulation stabilizers applied did not have any effect on the behavior of the selected clear and cloudy beverages or water in combination with the mixture of antimicrobial glycolipids, i.e. observed increase in turbidity or disturbance of the emulsions, respectively, over time was unchanged.

It has now been surprisingly found that cyclodextrins, especially alpha-cyclodextrin, and polysorbates significantly improve the compatibility of the antimicrobial glycolipids with water based products. Addition of cyclodextrins and/or polysorbates allows for application of antimicrobial glycolipids even in those water based products where compatibility has shown to be limited, e.g. due to precipitation, occurrence of cloudiness, or increase in turbidity within 2 weeks after addition of antimicrobial glycolipids of formula I in selected clear and cloudy beverages.

Cyclodextrins and/or polysorbates in combination with antimicrobial glycolipids prevent increase of turbidity or formation of cloudiness in clear beverages and further prevent disturbance of the emulsion system of turbid beverages, thereby assuring long lasting compatibility for the shelf life of the water based products. Even more surprisingly, such combinations of antimicrobial glycolipids and mixtures thereof together with cyclodextrins and/or polysorbates fairly retain the antimicrobial efficacy of antimicrobial glycolipids at adequate use concentrations. Thus, cyclodextrins and/or polysorbates can be used as formulation stabilizers allowing for a much broader application of antimicrobial glycolipids and mixtures thereof in water based products while maintaining their desired antimicrobial efficacy.

Such combinations of antimicrobial glycolipids and mixtures thereof together with the said formulation stabilizers, i.e. cyclodextrins and polysorbates, are preferred in water based products, which are stable clear solutions or stable emulsions, respectively, for which an anti-microbial agent is needed for product performance. Such anti-microbial combinations are most preferred for preserving of clear or emulsified beverages against microbial spoilage.

The antimicrobial glycolipid according to general formula (I) (for the purpose of the specification also abbreviated as "antimicrobial glycolipid") can be regarded as being composed of two subunits: (a) the linear carboxylic acid defined by general formula (I) and by indices m, n, o and p, as well as (b) the carbohydrate moiety R.

Preferably, the subunit of the linear carboxylic acid comprises at least 20 carbon atoms, preferably 22 to 28 carbon atoms, more preferably 24 to 26 carbon atoms, in particular 26 carbon atoms.

Preferably, the carbohydrate moiety K is a trisaccharide which preferably comprises one or more xylopyranose moieties and/or one or more glucopyranose moieties.

Preferably, the carbohydrate moiety R is a moiety of the subformula

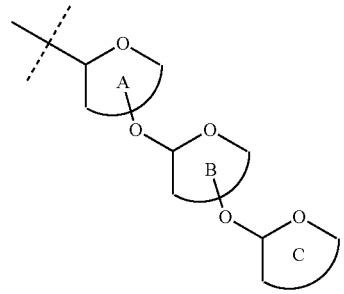

wherein the rings A, B and C are monosaccharide moieties each independently from the others with 5 or 6 ring members, wherein one or more of the hydroxyl groups may be acylated. Preferably, rings A and B are xylopyranose moieties and ring C is a glucopyranose moiety.

In particularly preferred embodiments, the carbohydrate moiety R has the following structure

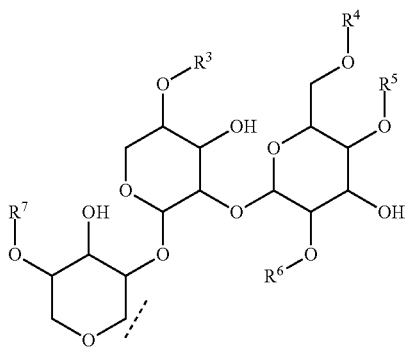

wherein $R^3$, $R^4$, $R^5$, $R^6$ and $R^7$ independently of one another mean —H or —C(=O)$C_1$-$C_6$-alkyl; wherein preferably at least one of $R^3$, $R^4$, $R^5$, $R^6$ and $R^7$ means —C(=O)$C_1$-$C_6$- alkyl, more preferably —C(=O)C$_3$-C$_6$-alkyl, most preferably —C(=O)isobutyl; and/or wherein preferably R$^6$ and R$^7$ mean —H.

The antimicrobial glycolipid according to general formula (I) can be present in form of an ester, i.e. may carry an ester functional group —C(=O)—O—. It is also possible that the antimicrobial glycolipid according to general formula (I) carries more than a single ester functional group, e.g. 2 or 3 ester functional groups.

The ester may be a lactone intramolecularly formed between the terminal carboxylic acid group of the subunit of the linear carboxylic acid with any of the hydroxyl groups of the subunit of the linear carboxylic acid or of the subunit of the carbohydrate moiety R.

Alternatively or additionally, any of the hydroxyl groups of the subunit of the linear carboxylic acid or of the subunit of the carbohydrate moiety R may be intermolecularly acylated, i.e. esterified, with a carboxylic acid, preferably with an aliphatic carboxylic acid, mote preferably with a C$_3$-C$_{10}$-alkanoic acid, especially with isovaleric acid. In preferred embodiments, 1 or 2 or 3 of the hydroxyl groups of the subunit of the linear carboxylic acid and/or of the subunit of the carbohydrate moiety R are acylated, i.e. esferified, with a carboxylic acid, preferably with an aliphatic carboxylic acid, wherein the carboxylic acids may be the same or different, preferably independently of one another selected from with a C$_1$-C$_{10}$-alkanoic acids, wherein preferably at least one of said carboxylic acids is a C$_3$-C$_{10}$-alkanoic acid, especially isovaleric acid.

Preferably, the carbohydrate moiety R carries at least one hydroxyl group esterified with an acid with 3 or more carbon atoms, especially wherein the acid is a C$_3$-C$_{10}$-alkanoic acid, especially isovaleric acid.

In particularly preferred embodiments, at least one antimicrobial glycolipid is according to general formula (II)

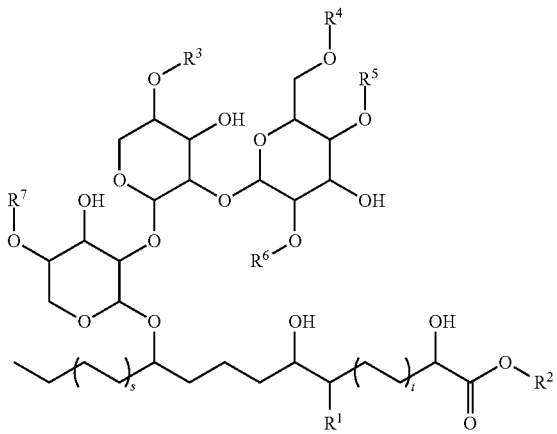

(II)

wherein
  s is 1 or 2;
  t is 6 or 7;
  R$^1$ means —H or —OH;
  R$^2$ means —H or —C$_1$-C$_6$-alkyl; preferably —H; and
  R$^3$, R$^4$, R$^5$, R$^6$ and R$^7$ independently of one another mean —H or —C(=O)C$_1$-C$_6$-alkyl.

In a preferred embodiment, at least one of R$^3$, R$^4$, R$^5$, R$^6$ and R$^7$ means —C(=O)C$_1$-C$_6$-alkyl, more preferably —C(=O)C$_3$-C$_{10}$-alkyl, most preferably —C(=O)isobutyl.

In preferred embodiments, R$^2$, R$^6$ and R$^7$ mean —H.

Preferably, at least one antimicrobial glycolipid is selected from compounds (II-A) to (II-D)

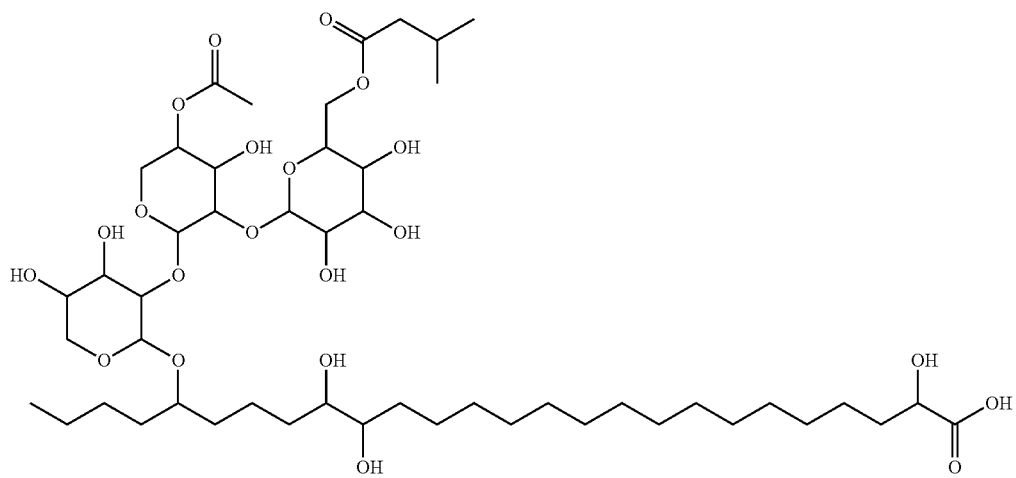

(II-A)

-continued

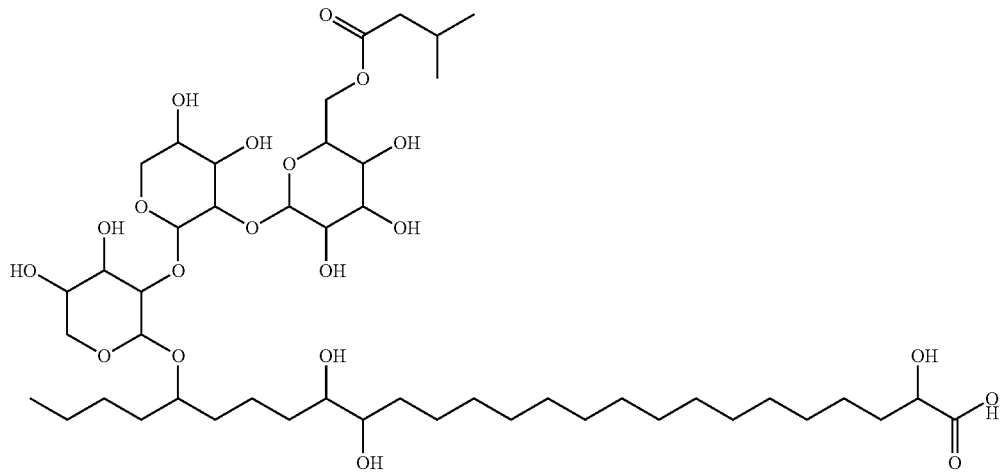

(II-B)

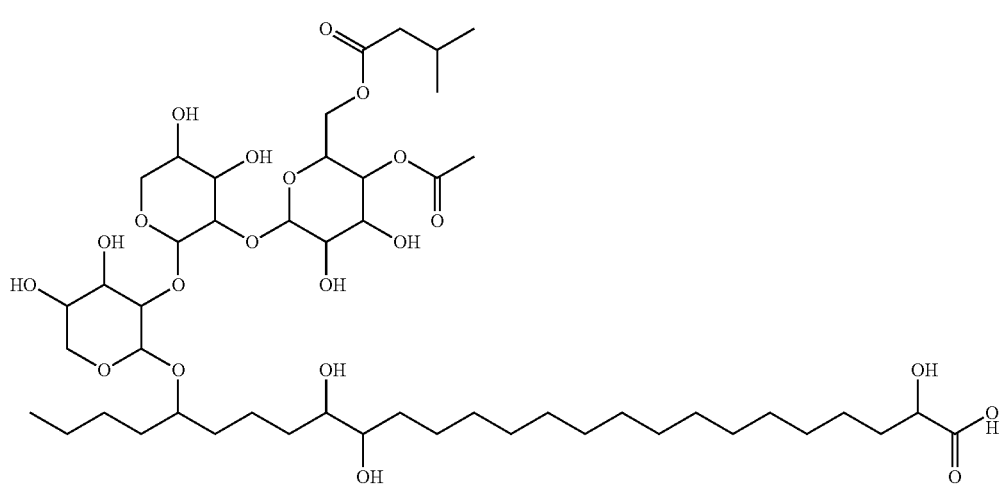

(II-C)

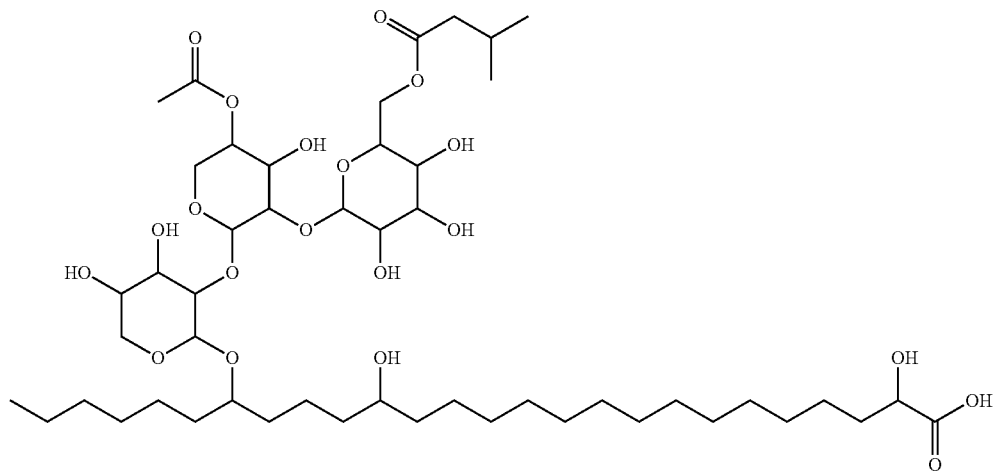

(II-D)

and the physiologically acceptable salts thereof.

The antimicrobial glycolipids, physiologically acceptable salts thereof, and/or esters thereof, are preferably provided in form of an extract from a natural source or are obtained from such an extract. Preferably, the source of the extract is a fungus belonging to family Dacrymycetaceae, a species of the genera *Dacryopinax, Ditiola, Guepiniopsis* and/or *Femsjonia*, more preferably *Dacryopinax spathularia, Dacry-*

*myces* sp., *Dacrymyces stillatus*, *Dacrymyces chrysocomus*, *Guepiniopsis buccina* and/or *Femsjonia luteo-alba* (=*Ditilia pezizaeformis*). Especially preferred are *Dacryopinax spathularia* strain MUCL 53181, *Dacryopinax spathularia* strain MUCL 53182, *Ditiola radicata* strain MUCL 53180, *Ditiola nuda* strain MUCL 53179, *Dacrymyces chrysocomus* strain CBS280.84 and *Femsjonia luteo-alba* (=*Ditioia pezizaeformis*) strain MUCL 53500.

*Dacryopinax spathularia* strain MUCL 53181 was found to be among the best strains so far for producing the antimicrobial glycolipids and mixtures of two or more antimicrobial glycolipids, particularly the antimicrobial glycolipids exhibiting the strongest antimicrobial activity against yeasts and molds.

In all cases this means that either only one antimicrobial glycolipid (in substantially pure form or as a direct extract or a further enriched extract) or a mixture of two or more antimicrobial glycolipids (which mixtures is preferred) can be present, e.g. in an extract or pharmaceutical, nutraceutical, cosmetic, food or beverage formulation according to the invention, or that it or they can be of use according to the invention.

Typical mixtures of antimicrobial glycolipids according to the invention are compiled in the table here below as preferred embodiments $M^1$ to $M^3$, where the individual antimicrobial glycolipids are characterized by their nominal molecular weight (all values in weight percent relative to the total amount of antimicrobial glycolipids according to general formula (I) that are contained in the mixture):

| Nominal molecular weight [Da] | $M^1$ | $M^2$ | $M^3$ |
|---|---|---|---|
| ~886 | 0-20 wt.-% | 0-10 wt.-% | 0-3 wt.-% |
| ~928 | 0-20 wt.-% | 0-15 wt.-% | 0-10 wt.-% |
| ~954 | 0-20 wt.-% | 0-30 wt.-% | 0-20 wt.-% |
| ~970 (e.g., either 2x acetyl or 1x isovaleryl) | 30-50 wt.-% | 20-60 wt.-% | 30-60 wt.-% |
| ~1012 (e.g. 2x acetyl and 1x isovaleryl) | 20-50 wt.-% | 10-60 wt.-% | 20-60 wt.-% |
| ~1054 | 5-10 wt.-% | 0-30 wt.-% | 0-20 wt.-% |

The differences of the nominal molecular weight are essentially due to different acyl substituents. The specific glycolipids used in the examples fall within embodiment M3.

Within the most preferred glycolipid mixture, glycolipids having a nominal molecular weight of –1012 Da are characterized by an isovalerate (i.e. 3-methylbutanoate) ester moiety on the terminal glucopyranoside ring. Different positions of 3-methylbutanoate and acetate at the glucopyranoside unit are possible and of equal preference:

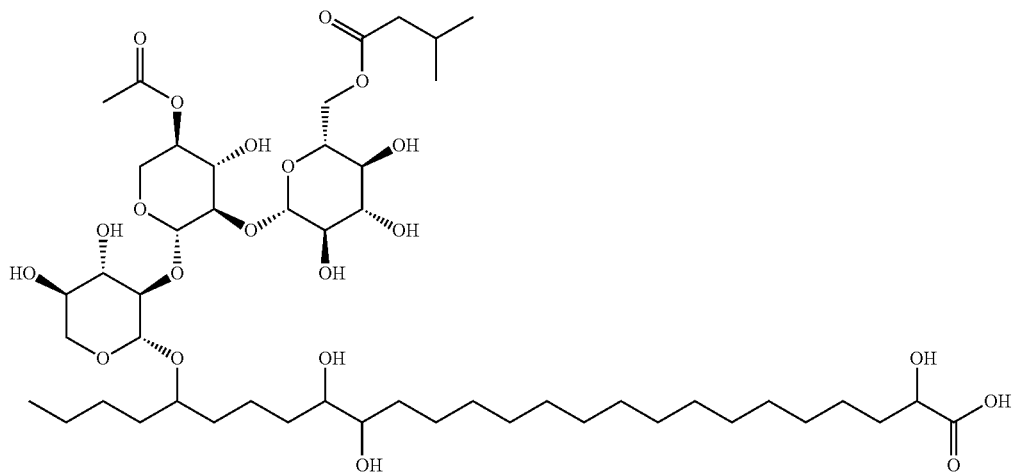 [SMILES: CCCCC(CCCC(O)C(O)CCCCCCCCCCCCCCC(O)C(=O)O)O[C@@H]1OC[C@@H](O)[C@H](O)[C@H]1O[C@@H]1OC[C@@H](OC(C)=O)[C@H](O)[C@H]1O[C@@H]1O[C@H](COC(=O)CC(C)C)[C@@H](O)[C@H](O)[C@H]1O]

Within the most preferred glycolipid mixture, glycolipids having a nominal molecular weight of –970 Da are characterized by either two acetate or one isovalerate moieties being attached as esters onto the trisaccharide moiety consisting of two xylopyranoside and one glucopyranoside moiety. (i.e. 3-methylbutanoate) ester moiety on the terminal glucopyranoside ring. When two acetate moieties are present, different positions of the acetyl moieties within the trisaccharide unit are possible and of equal preference:

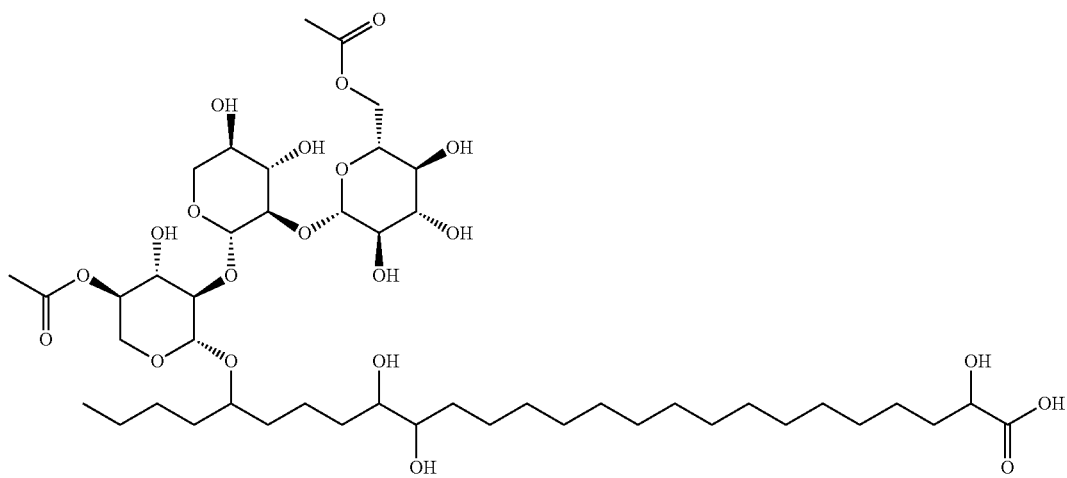 [SMILES: CCCCC(CCCC(O)C(O)CCCCCCCCCCCCCCC(O)C(=O)O)O[C@@H]1OC[C@@H](OC(C)=O)[C@H](O)[C@H]1O[C@@H]1OC[C@@H](O)[C@H](O)[C@H]1O[C@@H]1O[C@H](COC(C)=O)[C@@H](O)[C@H](O)[C@H]1O]

Likewise, different positions of 3-methylbutanoate at the glucopyranoside unit are possible and of equal preference:

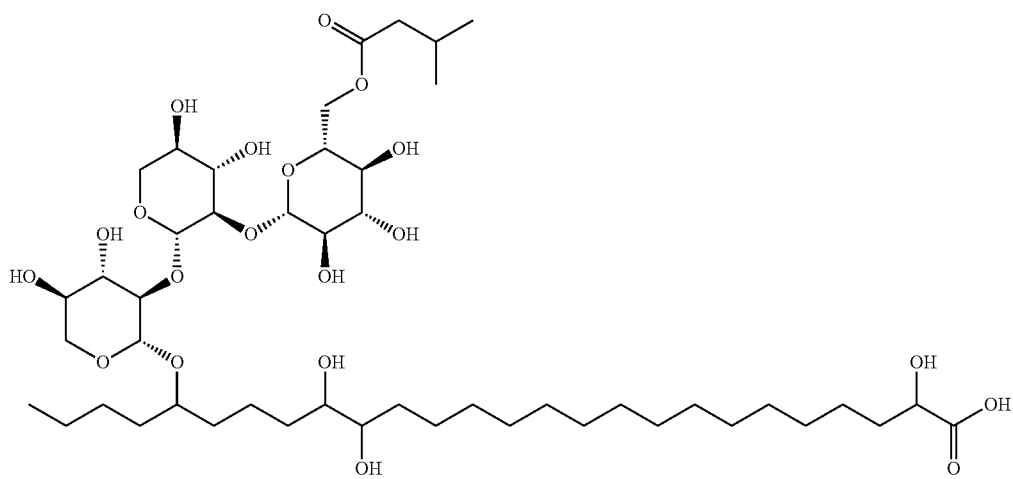 [SMILES: CCCCC(CCCC(O)C(O)CCCCCCCCCCCCCCC(O)C(=O)O)O[C@@H]1OC[C@@H](O)[C@H](O)[C@H]1O[C@@H]1OC[C@@H](O)[C@H](O)[C@H]1O[C@@H]1O[C@H](COC(=O)CC(C)C)[C@@H](O)[C@H](O)[C@H]1O]

The relative weight ratio of said formulation component, preferably alpha-cyclodextrin, to said glycolipid component is within the range of from 100:1 to 1:2, preferably 10:1 to 1:1, more preferably 7.5:1 to 1.5:1, still more preferably 6:1 to 2:1, yet more preferably 5:1 to 2.5:1, based on the total weight of all antimicrobial glycolipids according to general formula (I) in the composition and based on the total weight of all formulation stabilizers in the composition.

The formulation component of the composition according to the invention comprises or consists of a formulation stabilizer, preferably alpha-cyclodextrin. The formulation stabilizer (=formulation enhancer) improves the compatibility of the glycolipid component in water based consumer products. Thus, for the purpose of the specification, the term "formulation stabilizer" preferably refers to an "enhancer of compatibility in water based formulations". Preferably, the "formulation stabilizer" is a "solubility enhancer" or a "dispersibility enhancer". Preferably, the "formulation stabilizer" stabilizes the glycolipid component to remain in solution and dispersion, respectively, i.e. prevents precipitation of the glycolipid component or prevents the composition to become cloudy or opaque, e.g. upon storage.

In a preferred embodiment of the invention, the formulation component comprises or consists of a formulation stabilizer selected from cyclodextrins, preferably alpha-cyclodextrin.

Cyclodextrins or cyclic dextrins belong to a well known family of compounds made up of sugar molecules bound together in a ring. Cyclodextrins may be obtained by enzymatic degradation of starch and are typically composed of 5 or more α-D-glucopyranoside units linked 1-to-4 glycosidic, as in amylose. Hence, they are sometimes also referred to as cycloamyloses. Most typical cyclodextrins contain a number of glucose monomers ranging from six to eight units in a ring, creating a cone shape, i.e. α (alpha)-cyclodextrin (6-membered sugar ring molecule), β (beta)-cyclodextrin (7-membered sugar ring molecule) and γ (gamma)-cyclodextrin (8-membered sugar ring molecule).

Alpha-cyclodextrin has been authorized for use as a soluble dietary fibre and is also used as solubility enhancer. Alpha-, beta-, and gamma-cyclodextrin are all generally recognized as safe (GRAS) by the FDA. Cyclodextrins generally are known to enhance the solubility and bioavailability of hydrophobic, i.e. poorly water soluble compounds, e.g. cholesterol or small aromatic compounds. However, the enhancement of compatibility of very well water soluble, non-hydrophobic antimicrobial glycolipids in water based products according to the present invention was not yet known to the public.

Preferably, the cyclodextrin according to the invention is selected from alpha-cyclodexirin (CAS RN 10016-20-3), beta-cyclodextrin (CAS RN 7585-39-9), hydroxypropyl-beta-cyclodextrin (128446-35-5) and methyl-beta-cyclodextrin (CAS RN 128446-36-6); whereas alpha-cyclodextrin, beta-cyclodextrin and methyl-beta-cyclodextrin are particularly preferred. Most preferred is the selection of alpha-cyclodextrin.

It has been found that highly branched cyclic dextrin and gamma cyclodextrin (CAS RN 17465-86-0) provide less pronounced beneficial effects and hence are less preferred.

Preferably, the relative weight ratio of said cyclodextrin, preferably alpha-cyclodextrin, to said glycolipid component is within the range of from 20:1 to 1:1; more preferably within the range of from 10:1 to 2.5:1; still more preferably from 7.5:1 to 2.5:1 or from 10:1 to 5:1; yet more preferably or from 7.5:1 to 5:1, or from 5:1 to 2.5:1.

In another preferred embodiment of the invention, the formulation component comprises or consists of a formulation stabilizer selected from polysorbates.

Polysorbates represent a class of oily liquids synthetically derived from PEG-ylated sorbitan (a derivative of sorbitol) esterified with fatty acids. Typical representatives comprise Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate) and Polysorbate 80 (polyoxyethylene (20) sorbitan monooleate). The number 20 following the 'polyoxyethylene' part refers to the total number of oxyethylene —($CH_2CH_2O$)— groups found in the molecule. The number following the 'polysorbate' part is related to the type of fatty acid associated with the polyoxyethylene sorbitan part of the molecule. Monolaurate is indicated by 20, monopalmitate is indicated by 40, monostearate by 60, and monooleate by 80.

Polysorbates are emulsifiers used in pharmaceuticals and food preparations. However, the enhancement of compatibility of very well water soluble antimicrobial glycolipids in water based products according to the present invention was not yet known to the public.

Preferably, the polysorbate according to the invention is selected from the group consisting of polysorbate 20 (polyoxyethylene-(20)-sorbitane monolaurate); polysorbate 21 (polyoxyethylene-(4)-sorbitane monolaurate); polysorbate 40 (polyoxyethylene-(20)-sorbitane monopalmitate); polysorbate 60 (polyoxyethylene-(20)-sorbitane monostearate); polysorbate 61 (polyoxyethylene-(4)-sorbitane monosteante); polysorbate 65 (polyoxyethylene-(20)-sorbitanetristearate); polysorbate 80 (polyoxyethylene-(20)-sorbitane monooleate); polysorbate 81 (polyoxyethylene-(5)-sorbitane monooleate); polysorbate 85 (polyoxyethylene-(20)-sorbitane trioleate); polysorbate 120 (polyoxyethylene-(20)-sorbitane monoisostearate); and a mixture of any of the foregoing, Polysorbate 60 and polysorbate 80 are preferred.

Preferably, the relative weight ratio of said polysorbate to said glycolipid component is within the range of from in the range of 50:1 to 4:1; more preferably in the range of from 20:1 to 8:1.

The composition according to the invention may be liquid, semisolid or solid, e.g. a powder.

The composition according to the invention may be a precursor of a beverage, especially a concentrate, a syrup or a powder.

Besides the glycolipid component the composition according to the invention may contain an additional preservative. Preferably, however, the glycolipid component is the only constituent of the composition exhibiting antimicrobial properties.

Another aspect of the invention relates to a material comprising, as or within a coating and/or as admixture, a composition according to the invention as described above. This material must be other than the fungus from which the compound or antimicrobial glycolipids are extracted. Preferably, the material is a cosmetic, a food, a beverage, a pharmaceutical, a home care, a medical device, or an active packaging material, especially a beverage, a beverage precursor, especially a concentrate, syrup or powder, a food or a cosmetic. In a preferred embodiment, such material comprises an additional preservative. In another preferred embodiment, such material comprises no additional preservative.

Another aspect of the invention relates to a material according to the invention as described above, which is obtained after heat treatment.

Another aspect of the invention relates to orally consumable water based product comprising the composition according to the invention as described above. All preferred embodiments that have been described above for the composition according to the invention also analogously apply to the orally consumable water based product according to the invention and are not repeated hereinafter.

Preferably, the orally consumable water based product is selected from cosmetics, foods, beverages, and pharmaceuticals, especially in the form of a powder or a liquid.

In preferred embodiments, the orally consumable water based product is a beverage selected from carbonated beverages, non-carbonated beverages, alcoholic beverages and non-alcoholic beverages.

Preferably, the content of the glycolipid component is within the range of from 0.0005 to 1 wt.-%; more preferably from 0.0005 to 0.1 wt.-%: still more preferably from 0.0005 to 0.05 wt.-%; and roost preferably from 0.0005 to 0.01 wt.-%; based on the total weight of the orally consumable water based product.

Preferably, the content of the formulation component, which preferably comprises or consists of alpha-cyclodextrin, is within the range of from 0.0012 to 5 wt.-%; more preferably from 0.0012 to 0.5 wt.-%; still more preferably from 0.0012 to 0.25 wt.-%; and most preferably from 0.0012 to 0.05 wt.-%; based on the total weight of the orally consumable water based product.

Preferably
the content of the glycolipid component is within the range of from 0.0005 to 1 wt.-%; more preferably from 0.0005 to 0.1 wt.-%; still more preferably from 0.001 to 0.1 wt.-% or from 0.0005 to 0.01 wt.-%; even more preferably from 0.005 to 0.05 wt.-%; based on the total weight of the orally consumable water based product; and/or
the content of the formulation component is within the range of from 030005 to 1 wt.-%; more preferably in the range of 0.001 to 0.1 wt.-%, still more preferably in the range of 0.005 to 0.05 wt.-%; even more preferably from 0.0012 to 0.5 wt.-%, or from 0.0012 to 0.25 wt.-%, or from 0.0025 to 0.5 wt.-%; or from 0.0025 to 0.5 wt.-%, or from 0.0025 to 0.25 wt.-%, or from 0.005 to 0.5 wt.-%; or from 0.0012 to 0.05 wt.-%, or from 0.0012 to 0.025 wt.-%, or from 0.0025 to 0.05 wt.-%; or from 0.012 to 0.25 wt.-%, or from 0.012 to 0.12 wt.-%, or from 0.025 to 0.25 wt.-%; based on the total weight of the orally consumable water based product. Preferably the content of the glycolipid component is within the range of from 3 so 100 ppmw (parts per million by weight); more preferably in the range of from 3 to 25 ppmw, of from 25 to 50 ppmw, or from 50 to 75 ppmw, or from 75 to 100 ppmw; even more preferably in the range of from 3 to 10 ppmw, or from 10 to 20 ppmw, or from 20 to 30 ppmw, or from 30 to 40 ppmw, or from 40 to 50 ppmw, or from 50 to 60 ppmw, or from 60 to 70 ppmw, or from 70 to 80 ppmw, or from 80 to 90 ppmw, or from 90 to 100 ppmw; based on the total weight of the orally consumable water based product; and/or the weight ratio of the formulation component, preferably comprising or consisting of alpha-cyclodextrin, to the glycolipid component is within the range of from 20:1 to 1:1; mere preferably within the range of from 10:1 to 2.5:1; still more preferably from 7.5:1 to 2.5:1 or from 10:1 to 5:1; yet more preferably or from 7.5:1 to 5:1, or from 5:1 to 2.5:1.

Preferably, the content of the glycolipid component in the orally consumable water based product depends upon the nature of the orally consumable water based product. It has been found that the following concentrations are preferred for the following orally consumable water based products:

Clear beverages (turbidity 0-10 NTU): 3-25 mg/L
Cloudy beverages (turbidity>10 NTU): 10-100 mg/L
Juices and fruit drinks with fruit content>50%: 50-200 mg/L.

Preferably, the content of the formulation component in the orally consumable water based product also depends upon the nature of the orally consumable water based product. Preferably, its content is 5-10-fold as compared to the glycolipid component (w/v), more preferably 8-10 fold, most preferably 10-fold. It has been found that the following concentrations are preferred for the following orally consumable water based products:

Clear beverages (turbidity 0-10 NTU): 10-200 mg/L
Cloudy beverages (turbidity>10 NTU): 50-1000 mg/L
Juices and fruit drinks with fruit content>50%: 250-2000 mg/L.

Preferably, the orally consumable water based product has a pH value within the range of 3.0±1.5, or 4.0±1.5, or 5.0±1.5, or 6.0±1.5.

In a preferred embodiment, the glycolipid component comprises or consists of an antimicrobial glycolipid according to Formula (II-A) or mixture thereof and the formulation component comprises or consists of a cyclodextrin, preferably alpha-cyclodextrin, wherein the concentration of the glycolipid component is preferably within the range of from 3 to 100 ppmw, relative to the total weight of the orally consumable water based product, and wherein the relative weight ratio of to formulation component, preferably alpha-cyclodextrin, to the glycolipid component is preferably within the range of from 2.5:1 to 5:1.

Further preferred embodiments $A^1$ to $A^{10}$ of such orally consumable water based product are summarized in the table here below:

| | $A^1$ | $A^2$ | $A^3$ | $A^4$ | $A^5$ | $A^6$ | $A^7$ | $A^8$ | $A^9$ | $A^{10}$ |
|---|---|---|---|---|---|---|---|---|---|---|
| | antimicrobial glycolipid | | | | | | | | | |
| type | (II-A) | (II-A) | (II-A) | (II-A) | (II-A) | (II-A) | (II-A) | (II-A) | (II-A) | (II-A) |
| concentration [µg/ml] | 10 ± 9 | 20 ± 18 | 30 ± 27 | 40 ± 36 | 50 ± 45 | 60 ± 54 | 70 ± 63 | 80 ± 72 | 90 ± 81 | 100 ± 90 |
| | formulation stabilizer | | | | | | | | | |
| type | a-CD | a-CD | a-CD | a-CD | a-CD | a-CD | a-CD | a-CD | a-CD | a-CD |
| concentration [µg/ml] | 50 ± 45 | 100 ± 90 | 150 ± 135 | 200 ± 180 | 250 ± 225 | 300 ± 270 | 350 ± 315 | 400 ± 360 | 450 ± 405 | 500 ± 450 |

(II-A) = antimicrobial glycolipid according to Formula (II-A) or mixture thereof
a-CD = alpha-cyclodextrin Further preferred embodiments $B^1$ to $B^{10}$ of such orally consumable water based product are summarized in the table here below:

| | $B^1$ | $B^2$ | $B^3$ | $B^4$ | $B^5$ | $B^6$ | $B^7$ | $B^8$ | $B^9$ | $B^{10}$ |
|---|---|---|---|---|---|---|---|---|---|---|
| | antimicrobial glycolipid | | | | | | | | | |
| type | (II-A) | (II-A) | (II-A) | (II-A) | (II-A) | (II-A) | (II-A) | (II-A) | (II-A) | (II-A) |
| concentration [µg/ml] | 10 ± 6 | 20 ± 12 | 30 ± 18 | 40 ± 24 | 50 ± 30 | 60 ± 36 | 70 ± 42 | 80 ± 48 | 90 ± 54 | 100 ± 60 |
| | formulation stabilizer | | | | | | | | | |
| type | a-CD | a-CD | a-CD | a-CD | a-CD | a-CD | a-CD | a-CD | a-CD | a-CD |
| concentration [µg/ml] | 50 ± 30 | 100 ± 60 | 150 ± 90 | 200 ± 120 | 250 ± 150 | 300 ± 180 | 350 ± 210 | 400 ± 240 | 450 ± 270 | 500 ± 300 |

(II-A) = antimicrobial glycolipid according to Formula (II-A) or mixture thereof
a-CD = alpha-cyclodextrin Further preferred embodiments $C^1$ to $C^{10}$ of such orally consumable water based product are summarized in the table here below:

|  | $C^1$ | $C^2$ | $C^3$ | $C^4$ | $C^5$ | $C^6$ | $C^7$ | $C^8$ | $C^9$ | $C^{10}$ |
|---|---|---|---|---|---|---|---|---|---|---|
| | | | | | antimicrobial glycolipid | | | | | |
| type | (II-A) | (II-A) | (II-A) | (II-A) | (II-A) | (II-A) | (II-A) | (II-A) | (II-A) | (II-A) |
| concentration [µg/ml] | 10 ± 3 | 20 ± 6 | 30 ± 9 | 40 ± 12 | 50 ± 15 | 60 ± 18 | 70 ± 21 | 80 ± 24 | 90 ± 27 | 100 ± 30 |
| | | | | | formulation stabilizer | | | | | |
| type | a-CD | a-CD | a-CD | a-CD | a-CD | a-CD | a-CD | a-CD | a-CD | a-CD |
| concentration [µg/ml] | 50 ± 15 | 100 ± 30 | 150 ± 45 | 200 ± 60 | 250 ± 75 | 300 ± 90 | 350 ± 105 | 400 ± 120 | 450 ± 135 | 500 ± 150 |

(II-A) = antimicrobial glycolipid according to Formula (II-A) or mixture thereof
a-CD = alpha-cyclodextrin In a preferred embodiment, the orally consumable water based product according to the invention is a clear carbonated soft drink or clear enhanced water. Preferably, the glycolipid component comprises or consists of an antimicrobial glycolipid according to Formula (II-A) or mixture thereof and the formulation component comprises or consists of a cyclodextrin, preferably alpha-cyclodextrin, wherein the concentration of the glycolipid component is preferably within the range of from 3 to 100 ppmw, relative to the total weight of the clear carbonated soft drink or clear enhanced water, and wherein the relative weight ratio of to formulation component, preferably alpha-cyclodextrin, to the glycolipid component is preferably within the range of from 2.5:1 to 5:1. Further preferred embodiments $D^1$ to $D^9$ of such carbonated soft drinks or enhanced waters are summarized in the table here below:

|  | $D^1$ | $D^2$ | $D^3$ | $D^4$ | $D^5$ | $D^6$ | $D^7$ | $D^8$ | $D^9$ |
|---|---|---|---|---|---|---|---|---|---|
| | | | | | antimicrobial glycolipid | | | | |
| type | (II-A) | (II-A) | (II-A) | (II-A) | (II-A) | (II-A) | (II-A) | (II-A) | (II-A) |
| concentration [µg/ml] | 3 ± 2 | 5 ± 2 | 10 ± 3 | 5 ± 2 | 10 ± 3 | 25 ± 7 | 5 ± 2 | 10 ± 3 | 25 ± 7 |
| | | | | | formulation stabilizer | | | | |
| type | a-CD | a-CD | a-CD | a-CD | a-CD | a-CD | b-CD | b-CD | b-CD |
| concentration [µg/ml] | 15 ± 4 | 25 ± 5 | 50 ± 10 | 50 ± 10 | 100 ± 20 | 250 ± 50 | 50 ± 10 | 100 ± 50 | 250 ± 50 |

(II-A) = antimicrobial glycolipid according to Formula (II-A) or mixture thereof
a-CD = alpha-cyclodextrin
b-CD = beta-cyclodextrin In another preferred embodiment, the orally consumable water based product according to the invention is a cloudy carbonated soft drink or a cloudy enhanced water. Preferably, the glycolipid component comprises or consists of an antimicrobial glycolipid according to Formula (II-A) or mixture thereof and the formulation component comprises or consists of a cyclodextrin, preferably alpha-cyclodextrin, wherein the concentration of the glycolipid component is preferably within the range of from 3 to 100 ppmw, relative to the total weight of the cloudy carbonated soft drink or cloudy enhanced water, and wherein the relative weight ratio of to formulation component, preferably alpha-cyclodextrin, to the glycolipid component is preferably within the range of from 2.5:1 to 5:1. Further preferred embodiments $E^1$ to $E^8$ of such carbonated soft drinks or enhanced waters are summarized in the table here below:

|  | $E^1$ | $E^2$ | $E^3$ | $E^4$ | $E^5$ | $E^6$ | $E^7$ | $E^8$ |
|---|---|---|---|---|---|---|---|---|
| | | | | antimicrobial glycolipid | | | | |
| type | (II-A) | (II-A) | (II-A) | (II-A) | (II-A) | (II-A) | (II-A) | (II-A) |
| concentration [µg/ml] | 10 ± 3 | 20 ± 5 | 10 ± 3 | 25 ± 7 | 50 ± 10 | 80 ± 20 | 10 ± 3 | 25 ± 7 |

|  | E¹ | E² | E³ | E⁴ | E⁵ | E⁶ | E⁷ | E⁸ |
|---|---|---|---|---|---|---|---|---|
|  | formulation stabilizer | | | | | | | |
| type | a-CD | a-CD | a-CD | a-CD | a-CD | a-CD | b-CD | b-CD |
| concentration [µg/ml] | 50 ± 10 | 100 ± 20 | 100 ± 20 | 250 ± 50 | 500 ± 100 | 800 ± 200 | 100 ± 20 | 250 ± 50 |

(II-A) = antimicrobial glycolipid according to Formula (II-A) or mixture thereof
a-CD = alpha-cyclodextrin
b-CD = beta-cyclodextrin In another preferred embodiment, the orally consumable water based product according to the invention is a clear energy drink or clear sport drink or clear tea ready to drink (RTD). Preferably, the glycolipid component comprises or consists of an antimicrobial glycolipid according to Formula (II-A) or mixture thereof and the formulation component comprises or consists of a cyclodextrin, preferably alpha-cyclodextrin, wherein the concentration of the glycolipid component is preferably within the range of from 3 to 100 ppmw, relative to the total weight of the clear energy drink or clear sport drink or clear tea ready to drink, and wherein the relative weight ratio of to formulation component, preferably alpha-cyclodextrin, to the glycolipid component is preferably within the range of from 2.5:1 to 5:1. Further preferred embodiments $F^1$ to $F^8$ of such energy drinks or sport drinks or tea RTD are summarized in the table here below:

|  | F¹ | F² | F³ | F⁴ | F⁵ | F⁶ | F⁷ | F⁸ |
|---|---|---|---|---|---|---|---|---|
|  | antimicrobial glycolipid | | | | | | | |
| type | (II-A) | (II-A) | (II-A) | (II-A) | (II-A) | (II-A) | (II-A) | (II-A) |
| concentration [µg/ml] | 10 ± 3 | 16 ± 4 | 10 ± 3 | 25 ± 7 | 50 ± 10 | 80 ± 20 | 10 ± 3 | 25 ± 7 |
|  | formulation stabilizer | | | | | | | |
| type | a-CD | a-CD | a-CD | a-CD | a-CD | a-CD | b-CD | b-CD |
| concentration [µg/ml] | 50 ± 10 | 80 ± 20 | 80 ± 20 | 200 ± 50 | 400 ± 100 | 650 ± 150 | 80 ± 20 | 200 ± 50 |

(II-A) = antimicrobial glycolipid according to Formula (II-A) or mixture thereof
a-CD = alpha-cyclodextrin
b-CD = beta-cyclodextrin In another preferred embodiment, the orally consumable water based product according to the invention is a cloudy energy drink or cloudy sport drink or cloudy tea ready to drink (RTD). Preferably, the glycolipid component comprises or consists of an antimicrobial glycolipid according to Formula (II-A) or mixture thereof and the formulation component comprises or consists of a cyclodextrin, preferably alpha-cyclodextrin, wherein the concentration of the glycolipid component is preferably within the range of from 3 to 100 ppmw, relative to the total weight of the cloudy energy drink or cloudy sport drink or cloudy tea ready to drink, and wherein the relative weight ratio of to formulation component, preferably alpha-cyclodextrin, to the glycolipid component is preferably within the range of from 2.5:1 to 5:1. Further preferred embodiments $G^1$ to $G^8$ of such energy drinks or sport drinks or tea RTD are summarised in the table here below:

|  | G¹ | G² | G³ | G⁴ | G⁵ | G⁶ | G⁷ | G⁸ |
|---|---|---|---|---|---|---|---|---|
|  | antimicrobial glycolipid | | | | | | | |
| type | (II-A) | (II-A) | (II-A) | (II-A) | (II-A) | (II-A) | (II-A) | (II-A) |
| concentration [µg/ml] | 15 ± 5 | 30 ± 8 | 15 ± 5 | 30 ± 10 | 50 ± 10 | 80 ± 20 | 10 ± 3 | 25 ± 7 |
|  | formulation stabilizer | | | | | | | |
| type | a-CD | a-CD | a-CD | a-CD | a-CD | a-CD | b-CD | b-CD |
| concentration [µg/ml] | 75 ± 15 | 150 ± 30 | 150 ± 30 | 300 ± 50 | 500 ± 100 | 800 ± 200 | 100 ± 20 | 250 ± 50 |

(II-A) = antimicrobial glycolipid according to Formula (II-A) or mixture thereof
a-CD = alpha-cyclodextrin
b-CD = beta-cyclodextrin In another preferred embodiment, the orally consumable water based product according to the invention is a clear fruit drink. Preferably, the glycolipid component comprises or consists of an antimicrobial glycolipid according to Formula (II-A) or mixture thereof and the formulation component comprises or consists of a cyclodextrin, preferably alpha-cyclodextrin, wherein the concentration of the glycolipid component is preferably within the range of from 3 to 100 ppmw, relative to the total weight of the clear fruit drink, and wherein the relative weight ratio of to formulation component, preferably alpha-cyclodextrin, to the glycolipid component is preferably within the range of from 2.5:1 to 5:1. Further preferred embodiments $H^1$ to $H^8$ of such fruit drinks are summarized in the table here below:

|  | $H^1$ | $H^2$ | $H^3$ | $H^4$ | $H^5$ | $H^6$ | $H^7$ | $H^8$ |
|---|---|---|---|---|---|---|---|---|
| antimicrobial glycolipid | | | | | | | | |
| type | (II-A) | (II-A) | (II-A) | (II-A) | (II-A) | (II-A) | (II-A) | (II-A) |
| concentration [µg/ml] | 10 ± 5 | 16 ± 4 | 10 ± 5 | 25 ± 7 | 50 ± 10 | 80 ± 20 | 25 ± 7 | 50 ± 15 |
| formulation stabilizer | | | | | | | | |
| typeE | a-CD | a-CD | a-CD | a-CD | a-CD | a-CD | b-CD | b-CD |
| concentration [µg/ml] | 50 ± 10 | 80 ± 20 | 80 ± 20 | 200 ± 50 | 400 ± 100 | 650 ± 150 | 250 ± 50 | 500 ± 100 |

(II-A) = antimicrobial glycolipid according to Formula (II-A) or mixture thereof
a-CD = alpha-cyclodextrin
b-CD = beta-cyclodextrin In another preferred embodiment, the orally consumable water based product according to the invention is a cloudy fruit drink. Preferably, the glycolipid component comprises or consists of an antimicrobial glycolipid according to Formula (II-A) or mixture thereof and the formulation component comprises or consists of a cyclodextrin, preferably alpha-cyclodextrin, wherein the concentration of the glycolipid component is preferably within the range of from 3 to 100 ppmw, relative to the total weight of the cloudy fruit drink, and wherein the relative weight ratio of to formulation component, preferably alpha-cyclodextrin, to the glycolipid component is preferably within the range of from 2.5:1 to 5:1. Further preferred embodiments $I^1$ to $I^8$ of such fruit drinks are summarized in the table here below:

|  | $I^1$ | $I^2$ | $I^3$ | $I^4$ | $I^5$ | $I^6$ | $I^7$ | $I^8$ |
|---|---|---|---|---|---|---|---|---|
| antimicrobial glycolipid | | | | | | | | |
| type | (II-A) | (II-A) | (II-A) | (II-A) | (II-A) | (II-A) | (II-A) | (II-A) |
| concentration [µg/ml] | 25 ± 7 | 50 ± 10 | 25 ± 7 | 50 ± 15 | 80 ± 20 | 120 ± 25 | 25 ± 7 | 50 ± 15 |
| formulation stabilizer | | | | | | | | |
| type | a-CD | a-CD | a-CD | a-CD | a-CD | a-CD | b-CD | b-CD |
| concentration [µg/ml] | 125 ± 25 | 250 ± 50 | 250 ± 50 | 500 ± 100 | 800 ± 200 | 1200 ± 250 | 250 ± 50 | 500 ± 100 |

(II-A) = antimicrobial glycolipid according to Formula (II-A) or mixture thereof
a-CD = alpha-cyclodextrin
b-CD = beta-cyclodextrin In yet another preferred embodiment, the orally consumable water based product according to the invention is fruit juice. Preferably, the glycolipid component comprises or consists of an antimicrobial glycolipid according to Formula (II-A) or mixture thereof and the formulation component comprises or consists of a cyclodextrin, preferably alpha-cyclodextrin, wherein the concentration of the glycolipid component is preferably within the range of from 3 to 100 ppmw, relative to the total weight of the fruit juice, and wherein the relative weight ratio of to formulation component, preferably alpha-cyclodextrin, to the glycolipid component is preferably within the range of from 2.5:1 to 5:1. Further preferred embodiments $J^1$ to $J^8$ of such fruit juice are summarized in the table here below:

|  | $J^1$ | $J^2$ | $J^3$ | $J^4$ | $J^5$ | $J^6$ | $J^7$ | $J^8$ |
|---|---|---|---|---|---|---|---|---|
| antimicrobial glycolipid | | | | | | | | |
| type | (II-A) | (II-A) | (II-A) | (II-A) | (II-A) | (II-A) | (II-A) | (II-A) |
| concentration [μg/ml] | 50 ± 10 | 80 ± 20 | 50 ± 10 | 80 ± 20 | 120 ± 20 | 170 ± 30 | 50 ± 10 | 80 ± 20 |
| formulation stabilizer | | | | | | | | |
| type | a-CD | a-CD | a-CD | a-CD | a-CD | a-CD | b-CD | b-CD |
| concentration [μg/ml] | 250 ± 50 | 400 ± 100 | 400 ± 100 | 640 ± 160 | 1000 ± 220 | 1450 ± 300 | 250 ± 50 | 500 ± 100 |

(II-A) = antimicrobial glycolipid according to Formula (II-A) or mixture thereof
a-CD = alpha-cyclodextrin
b-CD = beta-cyclodextrin In a preferred embodiment, the orally consumable water based product according to the invention is a oral care product. Preferably, the glycolipid component comprises or consists of an antimicrobial glycolipid according to Formula (II-A) or mixture thereof and the formulation component comprises or consists of a cyclodextrin, preferably alpha-cyclodextrin, wherein the concentration of the glycolipid component is preferably within the range of from 3 to 100 ppmw, relative to the total weight of the oral care product, and wherein the relative weight ratio of to formulation component, preferably alpha-cyclodextrin, to the glycolipid component is preferably within the range of from 2.5:1 to 5:1. Further preferred embodiments $K^1$ to $K^8$ of such oral care product are summarized in the table here below:

|  | $K^1$ | $K^2$ | $K^3$ | $K^4$ | $K^5$ | $K^6$ | $K^7$ | $K^8$ |
|---|---|---|---|---|---|---|---|---|
| antimicrobial glycolipid | | | | | | | | |
| type | (II-A) | (II-A) | (II-A) | (II-A) | (II-A) | (II-A) | (II-A) | (II-A) |
| concentration [μg/ml] | 50 ± 10 | 80 ± 20 | 50 ± 10 | 80 ± 20 | 120 ± 20 | 170 ± 30 | 50 ± 10 | 80 ± 20 |
| formulation stabilizer | | | | | | | | |
| type | | | a-CD | a-CD | a-CD | a-CD | b-CD | b-CD |
| concentration [μg/ml] | 250 ± 50 | 400 ± 100 | 400 ± 100 | 640 ± 160 | 1000 ± 220 | 1450 ± 300 | 250 ± 50 | 500 ± 100 |

(II-A) = antimicrobial glycolipid according to Formula (II-A) or mixture thereof
a-CD = alpha-cyclodextrin
b-CD = beta-cyclodextrin Is another preferred embodiment, the orally consumable water based product according to the invention is a carbonated soft drink or enhanced water. Preferred embodiments $L^1$ to $L^6$ of such carbonated soft drinks or enhanced waters are summarized in the table here below:

|  | $L^1$ | $L^2$ | $L^3$ | $L^4$ | $L^5$ | $L^6$ |
|---|---|---|---|---|---|---|
| antimicrobial glycolipid | | | | | | |
| type | (II-A) | (II-A) | (II-A) | (II-A) | (II-A) | (II-A) |
| concentration [μg/ml] | 5 ± 2 | 10 ± 3 | 25 ± 7 | 5 ± 2 | 10 ± 3 | 25 ± 7 |
| formulation stabilizer | | | | | | |
| type | PS60 | PS60 | PS60 | PS80 | PS80 | PS80 |
| concentration [μg/ml] | 40 ± 10 | 80 ± 20 | 200 ± 50 | 40 ± 10 | 80 ± 20 | 200 ± 50 |

(II-A) = antimicrobial glycolipid according to Formula (II-A) or mixture thereof
PS60 = polysorbate 60
PS80 = polysorbate 80

In another preferred embodiment, the orally consumable water based product according to the invention is an energy drink or sport drink or tea ready so drink (RTD). Preferred embodiments $M^1$ to $M^6$ of such energy drinks or sport drinks or Tea ready to drinks are summarized in the table here below:

|  | $M^1$ | $M^2$ | $M^3$ | $M^4$ | $M^5$ | $M^6$ |
|---|---|---|---|---|---|---|
| antimicrobial glycolipid | | | | | | |
| type | (II-A) | (II-A) | (II-A) | (II-A) | (II-A) | (II-A) |
| concentration [µg/ml] | 10 ± 3 | 25 ± 7 | 50 ± 10 | 10 ± 3 | 25 ± 7 | 50 ± 10 |
| formulation stabilizer | | | | | | |
| type | PS60 | PS60 | PS60 | PS80 | PS80 | PS80 |
| concentration [µg/ml] | 100 ± 20 | 250 ± 50 | 500 ± 100 | 100 ± 20 | 250 ± 50 | 500 ± 100 |

(II-A) = antimicrobial glycolipid according to Formula (II-A) or mixture thereof
PS60 = polysorbate 60
PS80 = polysorbate 80

In another preferred embodiment, the orally consumable water based product according to the invention is a fruit drink. Preferred embodiments $N^1$ to $N^6$ of such fruit drinks are summarized in the table here below:

|  | $N^1$ | $N^2$ | $N^3$ | $N^4$ | $N^5$ | $N^6$ |
|---|---|---|---|---|---|---|
| antimicrobial glycolipid | | | | | | |
| type | (II-A) | (II-A) | (II-A) | (II-A) | (II-A) | (II-A) |
| concentration [µg/ml] | 10 ± 3 | 25 ± 7 | 50 ± 10 | 10 ± 3 | 25 ± 7 | 50 ± 10 |
| formulation stabilizer | | | | | | |
| type | PS60 | PS60 | PS60 | PS80 | PS80 | PS80 |
| concentration [µg/ml] | 100 ± 20 | 250 ± 50 | 500 ± 100 | 100 ± 20 | 250 ± 50 | 500 ± 100 |

(II-A) = antimicrobial glycolipid according to Formula (II-A) or mixture thereof
PS60 = polysorbate 60
PS80 = polysorbate 80

In a preferred embodiment, the orally consumable water based product according to the invention is a oral care product. Preferred embodiments $O^1$ to $O^6$ of such oral care product are summarized in the table here below:

|  | $O^1$ | $O^2$ | $O^3$ | $O^4$ | $O^5$ | $O^6$ |
|---|---|---|---|---|---|---|
| antimicrobial glycolipid | | | | | | |
| type | (II-A) | (II-A) | (II-A) | (II-A) | (II-A) | (II-A) |
| concentration [µg/ml] | 10 ± 3 | 25 ± 7 | 50 ± 10 | 10 ± 3 | 25 ± 7 | 50 ± 10 |
| formulation stabilizer | | | | | | |
| type | PS60 | PS60 | PS60 | PS80 | PS80 | PS80 |
| concentration [µg/ml] | 100 ± 20 | 250 ± 50 | 500 ± 100 | 100 ± 20 | 250 ± 50 | 500 ± 100 |

(II-A) = antimicrobial glycolipid according to Formula (II-A) or mixture thereof
PS60 = polysorbate 60
PS80 = polysorbate 80

Another aspect of the invention relates to the use of a composition according to the invention as described above for preserving an orally consumable water based product according to the invention as described above. Preferably, the purpose of use is for enhancing the stability against microorganisms, especially where at least one microorganism is selected from the group consisting of mold, yeast and bacteria.

Preferably, the composition according to the invention is useful and used as a preservative or antimicrobial composition for a pharmaceutical, a medical device, a food container, a beverage container, or especially a food, a beverage, a cosmetic, or a home care product.

In a preferred embodiment, the composition according to the invention is useful and used as a biofilm inhibiting agent. It may be used as such by administering, or in methods comprising administering, one or more antimicrobial glycolipids, or a composition comprising it, to surfaces or materials coming into contact with surfaces. This way biofilms on various materials including medical devices, teeth, containers, home care products, pipes or mains or other liquid conducting or containing devices and the like can be avoided.

Another aspect of the invention relates to a method of enhancing microbial stability of a material, comprising adding to said material the composition according to the invention as described above, wherein said material is preferably selected from the group consisting of a cosmetic, a food, a beverage, a pharmaceutical, a home care, a medical device, and an active packaging material, especially a beverage, or a food, or a cosmetic, more preferably an orally consumable water based product according to the invention as described above.

Another aspect of the invention relates to a process for preparing an orally consumable water based product according to the invention as described above comprising the step of dissolving a composition according to the invention as described above in water or in an aqueous formulation.

Antimicrobial glycolipids or a mixture thereof can be applied in combination with cyclodextrins and/or polysorbates, i.e. the formulation stabilizer, by separately mixing both components, the antimicrobial glycolipids and one or more of the formulation stabilizer(s), within the water based product during its production or thereafter. Alternatively, antimicrobial glycolipids and the formulation stabilizer(s) can be blended as a ready to use combination independently to be applied as a fixed combination in water based products.

Since cyclodextrins as well as antimicrobial glycolipids or a mixture thereof are solid materials, one can mix the dried powders at different ratios generating powder mixtures which subsequently can be used directly by dissolving such powder mixtures within the water based product.

A highly concentrated solution of cyclodextrins in water is alternatively possible as a vehicle for application wherein the antimicrobial glycolipids or a mixture thereof is dissolved as well at defined concentrations. Such solutions of cyclodextrins and antimicrobial glycolipids can be directly added to water based products during their production.

Since polysorbates are liquid materials, a highly concentrated solution in water is always preferred wherein the antimicrobial glycolipids or a mixture thereof is dissolved as well at defined concentrations. Such solutions of polysorbates and antimicrobial glycolipids can be directly added to water based products during their production.

The following Examples illustrate the invention but are not to be construed as limiting its scope.

EXAMPLES

Preparation of Compositions

A glycolipid mixture with the following weight distribution was used:

| Glycolipid Nominal molecular weight [Da] | * |
|---|---|
| ~886 | 0.4% |
| ~928 | 4.6% |
| ~954 | 5.8% |
| ~970 (e.g., either 2x acetyl or 1x isovaleryl) | 41.9% |
| ~1012 (e.g. 2x acetyl and 1x isovaleryl) | 32.3% |
| ~1054 | 7.7% |
| Other glucolipids | 7.3% |

* relative wt. % of all glycolipids in sample.

The total glycolipid content in sample was 95 wt. % of dry mass.

Example 1: Water Based Stock Compositions of alpha-cyclodextrin and a Mixture of Antimicrobial Glycolipids Alpha-cyclodextrin (a-CD) and a mixture of antimicrobial glycolipids according to general formula (I) were poured into a glass vessel as solid materials as to generate a volume of 3 mL stock composition in relative quantities as outlined in the table below:

| Constituents | 1-1 | 1-2 | 1-3 | 1-4 | 1-5 |
|---|---|---|---|---|---|
| Alpha-cyclodextrin | 10 g/L | 50 g/L | 50 g/L | 50 g/L | 50 g/L |
| Mixture of antimicrobial glycolipids | 4 g/L | 6.7 g/L | 5 g/L | 12.5 g/L | 10 g/L |

Thus, for 3 mL of stock composition e.g. 1-1, 30 mg alpha-cyclodextrin and 12 mg mixture of antimicrobial glycolipids were employed. Subsequently, 3 mL demineralized water were added as to generate four stock compositions with different relative concentrations as indicated. The resultant stock, compositions were intensively stirred with a magnetic stirrer at room temperature for 30 min. to yield white slightly turbid compositions ready for use.

Example 2: Solid Powder Mixtures of alpha-cyclodextrin and a Mixture of Antimicrobial Glycolipids 1 g of alpha-cyclodextrin powder was poured into two 60 mL glass containers each. Subsequently, a mixture of antimicrobial glycolipids according to general formula (I) (milled with mesh size 0.5 mm) was added in amounts of 1 g and 0.4 g, respectively, as to yield the mass distribution outlined in the table below:

| Constituents | 2-1 | 2-2 |
|---|---|---|
| Alpha-cyclodextrin | 71.4 wt.-% | 50 wt.-% |
| Mixture of antimicrobial glycolipids | 28.6 wt.-% | 50 wt.-% |

The glass container was sealed and continuously shaken for 10 min, at room temperature yielding an optically homogeneous mixture of the two powders.

Example 3: Water Based Stock Compositions of Polysorbate 80 and a Mixture of Antimicrobial Glycolipids 4 g (4 ml) polysorbate 80 (PS80) were poured into three 60 mL glass containers each and mixed with 40 mL demineralized water. The compositions were intensively stirred with a magnetic stirrer at room temperature for 30 min. In three separate containers 0.4 g, 1 g and 1.6 g mixture of antimicrobial glycolipids according to general formula (I) were poured and subsequently given into the three polysorbate 80 solutions each. The stock compositions had the following concentrations:

| Constituent | 3-1 | 3-2 | 3-3 |
|---|---|---|---|
| Polysorbate 80 | 80 g/L | 80 g/L | 80 g/L |
| Mixture of antimicrobial glycolipids | 8 g/L | 20 g/L | 32 g/L |

The separate containers were washed with 2×3 mL demineralized water and this wash water was also poured into the three combined polysorbate 80 solutions each. The volume of each composition was adjusted to 50 mL by addition of water. The three glass containers were sealed, shaken and subsequently intensively stirred using a magnet stirrer at highest speed to yield a ready for use clear ivory coloured stock composition.

Performance of Compositions

Example 4: Screening for Suitable Formulation Enhancing Agents Used in Combination with Mixture of Antimicrobial Glycolipids As to identify formulation stabilizer a screening was conducted in which additives typically used in food, cosmetic or medical applications were combined with a mixture of antimicrobial glycolipids in a water based formulation. A rather high concentration of 1000 mg/l for the formulation enhancing agents was used as to not miss potential effects whereas the mixture of antimicrobial glycolipids was applied in typical use concentrations, i.e. 5, 10 and 25 µg/ml.

A total number of 36 additives were investigated as listed: Xanthan, Guar gum, Pektin, Polyvinylpolypyrrolidone, Glucuronolacton, beta-Cyclodextrin, Sorbitan monostearate, Pektin, Sorbitan monolaurate, Polysorbat 80, Glycocholat, myo-Inositol, Polyethylenglycol, Gum arabic, Locust bean gum, Agar, Alpha-Cyclodextrin, λ-Carrageen, κ-Carrageen, Konjac Gum, Tara Gum, Lecithin (from eggs), Lecithin (from soy beans), EDTA, Polyvinylpyrrolidone, Saccharoseacetatisobutyrate (SAIB), Methylcellulose, Hydroxypropylcellulose, Glycerol ester of wood rosin, Carboxymethylcellulose, Sodium alginate, Traganth, Polysorbat 20, Polysorbat 60, Lyso-Lecithin.

Portions of about 50 mL each for two beverages. "Gerolsteiner Orangenlimonade" (turbid orange lemonade, degassed; cloudy beverage) and "REWE Apfelsaft" (clear apple juice, sterile filtered; clear beverage) as well as for 10 mM citrate buffer is water (pH 3.0), were mixed each with aliquots of a mixture of antimicrobial glycolipids and the respective additives as to establish for each individually screened additive three combinations of concentrations (1000 µg/ml (with few exceptions as listed below) additive with 5, 10 and 25 µg/ml mixture of antimicrobial glycolipids, respectively); three controls with neither adding a mixture of antimicrobial glycolipids nor additive were run in parallel.

The necessary aliquots of a mixture of antimicrobial glycolipids were transferred from an aqueous stock solution containing 1 mg/ml mixture of antimicrobial glycolipids into the nine test solutions prepared for each additive.

The necessary aliquots of additives were transferred directly into the 50 mL portions.

For measurement of the turbidity the turbidity infrared device AL250T-IR from AQUALYTIC® was used. It was measured at three time points: day 0, 3, 7. All test samples were stored and handled at room temperature.

A qualitative overview on all additives tested for formulation stabilising effects in using a mixture of antimicrobial glycolipids in three water based product formulation, citrate buffer pH 3, orange lemonade and apple juice is given in the table below. In addition, the influence of the additives on the MIC of a mixture of antimicrobial glycolipids is described qualitatively. Also the effect of the additive itself on the water based products applied is described independent form the influence and interdependencies with a mixture of antimicrobial glycolipids.

| Component | Conc. of additive (mg/ml) | Effect of additive itself on water based product | 10 mM citrate buffer (pH 3) | Cloudy orange lemonade | Clear apple juice | Effect on MIC |
| --- | --- | --- | --- | --- | --- | --- |
| Guar gum | 1 | | nd | nd | n | n |
| Pektin (from apple) | 1 | Increase of turbidity | ic | ic | nd | n |
| Glucuronolacton | 1 | | n | n | n | n |
| Beta-Cyclodextrin | 1 | | ic | n | ic | lw |
| Sorbitan monostearate | 0.1 | Weakly soluble | dc | dc | n | sw |
| Pektin (from citrus) | 1 | Increase of turbidity | ic | n | ic | n |
| Sorbitan monolaurate | 1 | | nd | nd | nd | n |
| Polysorbate 80 | 1 | Increase of turbidity | ic | ic | ic | lw |
| Glycocholat | 1 | not compatible with orange lemonade | n | n | n | n |
| myo-Inositol | 1 | | dc | n | dc | n |
| Polyethylenglycol | 1 | | n | n | n | n |
| Gum arabic | 0.125 | | ic | n | nd | nd |
| Gum arabic from acacia tree | 1 | | dc | n | n | n |
| Locust bean gum | | Not soluble | | | | nd |
| Agar | 1 | | nd | n | nd | n |
| alpha-Cyclodextrin | 1 | | ic | ic | ic | lw |
| λ-Carrageen | 1 | Increase of turbidity | dc | n | n | n |
| κ-Carrageen | 1 | Precipitation | n | n | n | n |
| Konjac Gum | 0.5 | Not completely dissolved | n | n | dc | n |
| Tara Gum | 0.5 | Not completely dissolved | dc | n | dc | n |
| Lecithin (from eggs) | 1 | Increase of turbidity, lipid precipitate and film at surface | dc | ic | dc | nd |
| Lecithin (from soy) | 1 | Increase of turbidity | dc | ic | dc | w |
| EDTA | 1 | | dc | n | n | Impr. |
| Pektin variant 3 | 1 | | n | n | n | n |
| Polyvinylpyrrolidone k12 | 1 | | dc | n | n | n |
| Polyvinylpyrrolidone k30 | 1 | | dc | n | dc | n |

-continued

| Component | Conc. of additive (mg/ml) | Effect of additive itself on water based product | 10 mM citrate buffer (pH 3) | Cloudy orange lemon-ade | Clear apple juice | Effect on MIC |
|---|---|---|---|---|---|---|
| Polyvinyl-pyrrolidone k90 | 1 | | dc | n | n | n |
| Saccharose-acetateisobutyrat | 0.2 | | dc | n | n | n |
| Methyl cellulose | 1 | | n | n | n | n |
| Hydroxypropyl cellulose | 1 | | dc | n | n | n |
| Glycerol ester of wood rosin | 0.2 | | nd | n | n | n |
| Carboxymethyl cellulose | 1 | | n | n | n | n |
| Sodium alginate | 1 | | n | n | n | n |
| Xanthan | 1 | Increase of turbidity and viscosity | ic | ic | ic | n |
| Xanthan variant 2 | 1 | Increase of turbidity and viscosity | ic | ic | ic | n |
| Xanthan variant 3 | 1 | Increase of turbidity and viscosity | ic | ic | ic | n |
| Traganth | 1 | | n | n | n | n |
| Polysorbate 80 | 1 | Not compatible with apple juice. Clear citrus lemonade used instead | ic | ic | ic | lw |
| Polysorbate 20 | 1 | Not compatible with apple juice. Clear citrus lemonade used instead | nd | ic | ic | lw |
| Polysorbate 60 | 1 | Not compatible with apple juice. Clear citrus lemonade used instead | nd | ic | ic | lw |
| Lyso-Lecithin | 1 | Strong increase of turbidity | nd | nd | ic | w |

Legend:
n = neutral,
w = weaker,
lw = little weaker,
sw = strongly weaker,
dc = decrease in compatibility,
ic = increase in compatibility,
nd = not clear or not determined,
impr = improved;

Since xanthan and pektin additive applied (as bolded is the above list) displayed promising formulation stabilizing effects in this initial testing at rather high concentrations, testing was repeated and effect observed for a longer period of time, i.e. >=14 days, under same conditions as described above. All experiments done and reported in duplicate.

Samples were compared against control (blank without addition of antimicrobial glycolipids or xanthan) It revealed that the compatibility improving effect of these additives fades out over time as illustrated for xanthan in the table below:

| | 25 µg/ml of mixture of antimicrobial glycolipids in Orange Lemonade | | | |
|---|---|---|---|---|
| time [d] | control | control | Xanthan 1 mg/ml | Xanthan 1 mg/ml |
| | | Results of the visual control | | |
| 0 | Turbid, no particles, no precipitate | Turbid, no particles, no precipitate | Same as control | Same as control |
| 7 | Turbid, no particles, no precipitate | Turbid, no particles, no precipitate | Same as control | Turbid, particles, some precipitation |
| 14* | Turbid, no particles, no precipitate | Turbid, no particles, no precipitate | Turbid, particles, strong precipitate | Turbid, particles, strong precipitate |

| | 25 µg/ml of mixture of antimicrobial glycolipids in Apple Juice | | | |
|---|---|---|---|---|
| time [d] | control | control | Xanthan 1 mg/ml | Xanthan 1 mg/ml |
| | | Results of the visual control | | |
| 0 | clear, no particles, no precipitate | clear, no particles, no precipitate | Weakly turbid, no particles, no precipitate | Weakly turbid, no particles, no precipitate |
| 7 | clear, no particles, no precipitate | clear, no particles, no precipitate | Weakly turbid, no particles, no precipitate | Weakly turbid, no particles, no precipitate |
| 14* | clear, no particles, no precipitate | clear, no particles, no precipitate | Clear with precipitation | Clear with precipitation |

*not further observed beyond day 14 since compatibility was disturbed already after 14 days.

Improvement of compatibility by xanthan and pektin was also investigated at lower concentrations, i.e. 5, 10, 50, 100, 250, 500 and 750 µg/ml. For pektin at least 500 µg/ml were required and for Xanthan at least 250 µg/ml to observe the desired effect in the said water based products as used here.

It can be concluded from the above experimental data that xanthans and pektin can be used to improve the formulation stabilization of a mixture of antimicrobial glycolipids in water based product formulations for a limited period of time less than 7 days. In case stability is required for a longer period of time, then other additives, in particular cyclodextrins and polysorbates are to be used.

Example 5: Application of Combinations of alpha-cyclodextrin and Mixture of Antimicrobial Glycolipids As to confirm the formulation stabilizer properties of alpha-cyclodextrin for the use of a mixture of antimicrobial glycolipids in water based products, in particular beverages, combinations of both components at different concentrations were investigated in two commercially available beverages which lack compatibility using a mixture of antimicrobial glycolipids alone, i.e. in the absence of alpha-cyclodextrin.

Portions of about 50 mL each for the two beverages, "Gerolstetner Orangenlimonade" (turbid orange lemonade, de-gassed; cloudy beverage) and "REWE Apfelsaft" (clear apple juice, sterile filtered; clear beverage), were mixed with aliquots of a mixture of antimicrobial glycolipids and alpha-cyclodextrin as to establish the depicted nine combinations of concentrations (4-2 to 4-4 and 4-6 to 4-11, respectively); two control solutions with neither adding a mixture of antimicrobial glycolipids nor alpha-cyclodextrin were run in parallel (4-1 and 4-5, respectively).

The necessary aliquots of a mixture of antimicrobial glycolipids were transferred from an aqueous stock solution containing 1 mg/ml mixture of antimicrobial glycolipids into the two beverages, "Gerolsteiner Orangenlimonade" and "REWE Apfelsaft", respectively.

The necessary aliquots of alpha-cyclodextrin were transferred from art aqueous stock solution containing 10 mg/ml of alpha-cyclodextin into the two beverages, "Gerolsteiner Orangenlimonade" and "REWE Apfelsaft", respectively.

For measurement of the turbidity the turbidity infrared device AL250T-IR from AQUALYTIC® was used. It was measured at three time points; day 0, 3, 7. All test samples were stored and handled at room temperature.

a) Orange Lemonade

| 25 µg/ml of mixture of antimicrobial glycolipids | | | |
|---|---|---|---|
| 4-1 | 4-2 | 4-3 | 4-4 |
| control | alpha-cyclodextrin 10 µg/ml | alpha-cyclodextrin 100 µg/ml | alpha-cyclodextrin 500 µg/ml |

Results of the turbidity measurements are summarized in the tables below:

| | 25 µg/ml of mixture of antimicrobial glycolipids | | | |
|---|---|---|---|---|
| | 4-1 | 4-2 | 4-3 | 4-4 |
| Time [d]/turbidity | control | 10 µg/ml | 100 µg/ml | 500 µg/ml |
| 0 | 346 NTU | 339 NTU | 345 NTU | 331 NTU |
| 3 | 299 NTU | 263 NTU | 293 NTU | 298 NTU |
| 7 | 242 NTU | nd | 232 NTU | 253 NTU | nd = not determined

Results of the visual control are summarized in the tables below:

| | 25 µg/ml of mixture of antimicrobial glycolipids | | | |
|---|---|---|---|---|
| Time [d] | 4-1 control | 4-2 10 µg/ml | 4-3 100 µg/ml | 4-4 500 µg/ml |
| 0 | Turbid, no particles, no precipitate | Same as control | Same as control | Same as control |
| 3 | Turbid, no particles, small precipitate | Strong turbidity and particles, precipitation | Same as control | Same as control |
| 7 | Turbid, no particles, small precipitate | nd | Strong turbidity and particles, precipitation | Same as control | b) Apple Juice

| 10 µg/ml of mixture of antimicrobial glycolipids (clear solution) | | | | | | |
|---|---|---|---|---|---|---|
| 4-5 | 4-6 | 4-7 | 4-8 | 4-9 | 4-10 | 4-11 |
| control | alpha-cyclodextrin 10 µg/ml | alpha-cyclodextrin 25 µg/ml | alpha-cyclodextrin 50 µg/ml | alpha-cyclodextrin 75 µg/ml | alpha-cyclodextrin 100 µg/ml | alpha-cyclodextrin 500 µg/ml |

Results of the turbidity measurements are summarized in the sables below:

| | 10 µg/ml of mixture of antimicrobial glycolipids | | | | | | |
|---|---|---|---|---|---|---|---|
| Time [d]/ turbidity | 4-5 control | 4-6 10 µg/ml | 4-7 25 µg/ml | 4-8 50 µg/ml | 4-9 75 µg/ml | 4-10 100 µg/ml | 4-11 500 µg/ml |
| 0 | 0.47 NTU | 1.55 NTU | 0.68 NTU | 0.63 NTU | 0.71 NTU | 0.70 NTU | 0.76 NTU |
| 3 | 0.49 NTU | 1.14 NTU | 0.81 NTU | 0.67 NTU | 0.61 NTU | 0.79 NTU | 0.79 NTU |
| 7 | 0.46 NTU | nd | 0.72 NTU | nd | nd | 0.82 NTU | nd | nd = not determined

Results of the visual control are summarized in the tables below:

| | 10 µg/ml of mixture of antimicrobial glycolipids | | | | | | |
|---|---|---|---|---|---|---|---|
| Time [d] | 4-5 control | 4-6 10 µg/ml | 4-7 25 µg/ml | 4-8 50 µg/ml | 4-9 75 µg/ml | 4-10 100 µg/ml | 4-11 500 µg/ml |
| 0 | clear, no particles, not precipitate | Same as control | Same as control | Same as control | Same as control | Same as control | Same as control |
| 3 | clear, no particles, not precipitate | Precipitation | Same as control | Same as control | Same as control | Same as control | Same as control |
| 7 | clear, no particles, not precipitate | nd | Clear, no particles, precipitation | nd | nd | Same as control | nd |

It can be concluded from the above experimental data that the 10 µg/ml solution of a mixture of antimicrobial glycolipids in the clear beverage Apple Juice can safely be stabilized by combining with 100 µg/ml alpha-cyclodextrin whereas amounts of 10-25 µg/ml alpha-cyclodextrin obviously are not yet sufficient due to the observed precipitation. As demonstrated in Example 9, the plain 10 μg/ml solution of a mixture of antimicrobial glycolipids in the clear beverage Apple Juice displayed precipitation already after 3 days. For the 25 μg/ml solution of mixture of antimicrobial glycolipids in the cloudy beverage Orange Lemonade safe stabilization can be achieved by adding 500 μg/ml alpha-cyclodextrin whereas amounts of 100 μg/mi alpha-cyclodextrin obviously are not yet sufficient due to the observed increase in turbidity and precipitation after 7 days. As demonstrated in Example 9, the plain 25 μg/ml solution of a mixture of antimicrobial glycolipids in the cloudy beverage Orange Lemonade displayed precipitation already after 3 days.

Example 6: Temperature Dependency of Application of Combinations of alpha-cyclodextrin and a Mixture of Antimicrobial Glycolipids Applying a similar protocol as outlined under Example 5, the temperature dependency of the effect on compatibility was observed for alpha-cyclodextrin in combination with a mixture of antimicrobial glycolipids for the clear beverage apple juice. However, for the concentration of 10 μg/ml of mixture of antimicrobial glycolipids three combination with alpha-cyclodextrin, 25 (6-1, 6-2, 6-9, 6-10, 6-17, 6-18), 75 (6-3, 6-4, 6-11, 6-12, 6-19, 6-20) and 100 μg/ml (6-5, 6-6, 6-13, 6-14, 6-21, 6-22) and for the concentration of 25 μg/ml of mixture of antimicrobial glycolipids only 100 μg/ml alpha-cyclodextrin (6-7, 6-8, 6-15, 6-16, 6-23, 6-24) was used all with two test points, respectively. Besides room temperature, also 6° C. and 40° C. were applied; in addition the time period of observation was extended to 14 days, yielding the following results:

| | 6° C. 10 μg/ml of mixture of antimicrobial glycolipids | | | | | | |
|---|---|---|---|---|---|---|---|
| time [d] | control | 6-1 25 μg/ml | 6-2 25 μg/ml | 6-3 75 μg/ml | 6-4, 75 μg/ml | 6-5, 100 μg/ml | 6-6, 100 μg/ml |
| 0 | clear, no particles, not precipitate | Slightly turbid, no particles, not precipitate | Slightly turbid, no particles, not precipitate | Same as control | Same as control | Same as control | Same as control |
| 7 | clear, no particles, not precipitate | Same as control | Same as control | Same as control | Same as control | Same as control | Same as control |
| 14 | clear, no particles, not precipitate | Same as control | Same as control | Same as control | Same as control | Same as control | Same as control |
| 21 | clear, no particles, not precipitate | clear, no particles, precipitate | clear, no particles, precipitate | Same as control | Same as control | Same as control | Same as control |
| 28 | clear, no particles, not precipitate | — | — | Same as control | Same as control | Same as control | Same as control |

| time | 6° C. 25 µg/ml of mixture of antimicrobial glycolipids | | |
|---|---|---|---|
| [d] | control | 6-7, 100 µg/ml | 6-8, 100 µg/ml |
| 0 | clear, no particles, not precipitate | Slightly turbid, no particles, not precipitate | Slightly turbid, no particles, not precipitate |
| 7 | clear, no particles, not precipitate | Slightly turbid, no particles, not precipitate | Slightly turbid, no particles, not precipitate |
| 14 | clear, no particles, not precipitate | Slightly turbid, no particles, not precipitate | Slightly turbid, no particles, not precipitate |
| 21 | clear, no particles, not precipitate | clear, no particles, precipitate | clear, no particles, precipitate |

| time | 20° C. 10 µg/ml of mixture of antimicrobial glycolipids | | | | | | |
|---|---|---|---|---|---|---|---|
| [d] | control | 6-9, 25 µg/ml | 6-10, 25 µg/ml | 6-11, 75 µg/ml | 6-12, 75 µg/ml | 6-13, 100 µg/ml | 6-14, 100 µg/ml |
| 0 | clear, no particles, not precipitate | Slightly turbid, no particles, not precipitate | Slightly turbid, no particles, not precipitate | Same as control | Same as control | Same as control | Same as control |
| 7 | clear, no particles, not precipitate | Slightly turbid, no particles, not precipitate | Slightly turbid, no particles, not precipitate | Same as control | Same as control | Same as control | Same as control |
| 14 | clear, no particles, not precipitate | nd | nd | Same as control | Same as control | Same as control | Same as control |
| 21 | clear, no particles, not precipitate | Slightly turbid, no particles, precipitate | Slightly turbid, no particles, precipitate | clear, slight precipitate | clear, slight precipitate | Same as control | Same as control |
|  | contaminated | — | — | clear, slight precipitate | clear, slight precipitate | Same as control | Same as control |

| time | 20° C. 25 µg/ml of mixture of antimicrobial glycolipids | | |
|---|---|---|---|
| [d] | control | 6-15, 100 µg/ml | 6-16, 100 µg/ml |
| 0 | clear, no particles, not precipitate | Slightly turbid, no particles, not precipitate | Slightly turbid, no particles, not precipitate |
| 7 | clear, no particles, not precipitate | Same as control | Same as control |
| 14 | clear, no particles, not precipitate | Slightly turbid, no particles, precipitate | Slightly turbid, no particles, precipitate |
| 21 | clear, no particles, not precipitate | Slightly turbid, no particles, precipitate | Slightly turbid, no particles, precipitate |

| time | 40° C. 10 µg/ml of mixture of antimicrobial glycolipids | | | | | | |
|---|---|---|---|---|---|---|---|
| [d] | control | 6-17, 25 µg/ml | 6-18, 25 µg/ml | 6-19, 75 µg/ml | 6-20, 75 µg/ml | 6-21, 100 µg/ml | 6-22, 100 µg/ml |
| 0 | clear, no particles, not precipitate | Slightly turbid, no particles, not precipitate | Slightly turbid, no particles, not precipitate | Same as control | Same as control | Same as control | Same as control |
| 7 | clear, no particles, not precipitate | Slightly turbid, no particles, not precipitate | Slightly turbid, no particles, not precipitate | Same as control | Same as control | Same as control | Same as control |

| | 40° C. 10 µg/ml of mixture of antimicrobial glycolipids | | | | | |
|---|---|---|---|---|---|---|
| time [d] | control | 6-17, 25 µg/ml | 6-18, 25 µg/ml | 6-19, 75 µg/ml | 6-20, 75 µg/ml | 6-21, 100 µg/ml | 6-22, 100 µg/ml |
| 14 | clear, no particles, not precipitate | Slightly turbid, no particles, slight precipitate | Slightly turbid, no particles, slight precipitate | clear, no particles, slight precipitate | clear, no particles, slight precipitate | Same as control | Same as control |
| 21 | clear, no particles, not precipitate | Slightly turbid, no particles, slight precipitate | Slightly turbid, no particles, slight precipitate | clear, no particles, slight precipitate | clear, no particles, slight precipitate | Same as control | Same as control |
| 28 | clear, no particles, not precipitate | — | — | clear, no particles, slight precipitate | clear, no particles, slight precipitate | Same as control | Same as control |

| time | 40° C. 25 µg/ml of mixture of antimicrobial glycolipids | | |
|---|---|---|---|
| [d] | control | 6-23, 100 µg/ml | 6-24, 100 µg/ml |
| 0 | clear, no particles, not precipitate | Slightly turbid, no particles, not precipitate | Slightly turbid, no particles, not precipitate |
| 7 | clear, no particles, not precipitate | Slightly turbid, no particles, not precipitate | Slightly turbid, no particles, not precipitate |
| 14 | clear, no particles, not precipitate | Particles, precipitate | Particles, precipitate |
| 21 | clear, no particles, not precipitate | Particles, precipitate | Particles, precipitate |

Is can be concluded from the above experimental data that the improvement of compatibility by adding alpha-cyclodextrin is temperature dependent. Surprisingly, improvement of compatibility is stronger at lower temperature in the order of 4° C.>room temperature>40° C.; lack of compatibility of 10 µg/ml mixture of antimicrobial glycolipids with apple juice can successfully avoided by adding only 75 µg/ml at 4° C. whereas at 40° C. 100 µg/ml are needed. This is in opposite to what is normally expected since solubility is typically increased at higher temperature. This confirms that the improvement of compatibility is not a simple solubility enhancement but an unexpected finding in opposite to the normal expectation of a person trained in the field. Also the improvement of compatibility, applying alpha-cyclodextrin, is long lasting >28 days using 10 µg/ml mixture of antimicrobial glycolipids. This is substantially different to pektin and xanthan, depicted in Experiment 4 where the compatibility improving effect faded out already after 7 to 14 days.

Example 7: Application of Combinations of beta-cyclodextrin and a Mixture of Antimicrobial Glycolipids As to confirm the compatibility improving properties of beta-cyclodextrin for the use of a mixture of antimicrobial glycolipids in water based products, in particular beverages, combinations of both components at different concentrations were investigated in two commercially available beverages which lack compatibility using a mixture of antimicrobial glycolipids alone, i.e. in the absence of beta-cyclodextrin.

Portions of about 50 mL each for the two beverages, "Gerolsteiner Orangenlimonade" (orange lemonade, de-gassed, cloudy beverage) and "REWE Apfelsaft" (apple juice, sterile filtered, clear beverage), were mixed with aliquots of a mixture of antimicrobial glycolipids and beta-cyclodextrin, using volumes as indicated in the table below, as to establish the ten combinations of concentrations; two control solutions wish neither adding a mixture of antimicrobial glycolipids nor beta-cyclodextrin, was run in parallel.

The necessary aliquots of a mixture of antimicrobial glycolipids were transferred from an aqueous stock solution containing 1 mg/ml mixture of antimicrobial glycolipids in the two beverages, "Gerolsteiner Orangenlimonade" and "REWE Apfelsaft", respectively.

The necessary aliquots of alpha-cyclodextrin were transferred from an aqueous stock solution containing 10 mg/ml mixture of alpha-cyclodextrin in the two beverages, "Gerolsteiner Orangenlimonade" and "REWE Apfelsaft", respectively.

For measurement of the turbidity the turbidity infrared device AL250T-IR from AQUALYTIC® was used. It was measured at three time points: day 0, 3, 7. All test samples were stored and handled at room temperature.

a) Orange Lemonade

| Combined liquids | 5-1 control | 25 µg/ml of mixture of antimicrobial glycolipids | | | | |
|---|---|---|---|---|---|---|
| | | 5-2 50 µg/ml beta-cyclodextrin | 5-3 100 µg/ml beta-cyclodextrin | 5-4 250 µg/ml beta-cyclodextrin | 5-5 500 µg/ml beta-cyclodextrin | 5-6 1 mg/ml beta-cyclodextrin |
| v Lemonade [ml] | 50 | 49.25 | 49 | 48.25 | 47 | 44.5 |
| v beta-cyclodextrin Stock [ml] | 0 | 0.25 | 0.5 | 1.25 | 2.5 | 5 |
| v mixture of antimicrobial glycolipids Stock [ml] | 0 | 1.25 | 1.25 | 1.25 | 1.25 | 1.25 |

Results of the turbidity measurements are summarized in the tables below:

| time [d] | 5-1 control | 25 µg/ml mixture of antimicrobial glycolipids in | | | | |
|---|---|---|---|---|---|---|
| | | 5-2 50 µg/ml | 5-3 100 µg/ml | 5-4 250 µg/ml | 5-5 500 µg/ml | 5-6 1000 µg/ml |
| 0 | 346 NTU | 342 NTU | 341 NTU | 339 NTU | 320 NTU | 298 NTU |
| 7 | 260 NTU | 212 NTU | 214 NTU | 219 NTU | 217 NTU | 220 NTU |

Results of the visual control are summarized in the tables below:

| time [d] | 5-1 control | 25 µg/ml mixture of antimicrobial glycolipids | | | | |
|---|---|---|---|---|---|---|
| | | 5-2 50 µg/ml | 5-3 100 µg/ml | 5-4 250 µg/ml | 5-5 500 µg/ml | 5-6 1000 µg/ml |
| 0 | Turbid, no particles, not precipitate | Same as control | Same as control | Same as control | Same as control | Same as control |
| 7 | Turbid, no particles, not precipitate | Little more precipitation | Little more precipitation | Little more precipitation | Little more precipitation | Little more precipitation | b) Apple Juice

| Combined liquids | 5-7 control | 10 µg/ml of mixture of antimicrobial glycolipids (clear solution) | | | | |
|---|---|---|---|---|---|---|
| | | 5-8 50 µg/ml beta-cyclodextrin | 5-9 100 µg/ml beta-cyclodextrin | 5-10 250 µg/ml beta-cyclodextrin | 5-11 500 µg/ml beta-cyclodextrin | 5-12 1 mg/ml beta-cyclodextrin |
| v apple juice [ml] | 50 | 49.25 | 49 | 48.25 | 47 | 44.5 |
| v beta-cyclodextrin Stock [ml] | 0 | 0.25 | 0.5 | 1.25 | 2.5 | 5 |
| v mixture of antimicrobial glycolipids Stock [ml] | 0 | 0.5 | 0.5 | 0.5 | 0.5 | 0.5 |

Results of the turbidity measurements are summarized in the tables below:

| | 10 µg/ml of mixture of antimicrobial glycolipids (clear solution) | | | | | |
|---|---|---|---|---|---|---|
| time [d] | 5-7 control | 5-8 50 µg/ml | 5-9 100 µg/ml | 5-10 250 µg/ml | 5-11 500 µg/ml | 5-12 1000 µg/ml |
| 0 | 0.43 NTU | 1.09 NTU | 0.98 NTU | 0.72 NTU | 0.69 NTU | 0.72 NTU |
| 7 | 0.45 NTU | 0.52 NTU | 0.54 NTU | nd | nd | nd |

Results of the visual control are summarized in the tables below:

| | 10 µg/ml of mixture of antimicrobial glycolipids (clear solution) | | | | | |
|---|---|---|---|---|---|---|
| time [d] | 5-7 control | 5-8 50 µg/ml | 5-9 100 µg/ml | 5-10 250 µg/ml | 5-11 500 µg/ml | 5-12 1000 µg/ml |
| 0 | clear, no particles, not precipitate | Same as control | Same as control | Same as control | Same as control | Same as control |
| 7 | clear, no particles, not precipitate | Little more precipitation | Little more precipitation | nd | nd | nd | nd = not determined

It can be concluded from the above experimental data that the 10 µg/ml solution of a mixture of antimicrobial glycolipids in the clear beverage Apple Juice can fairly be stabilized by combining with 50 µg/ml beta-cyclodextrin. As demonstrated in Example 7, the plain 10 µg/ml solution of a mixture of antimicrobial glycolipids in the clear beverage Apple Juice displayed precipitation already after 3 days. For the 25 µg/ml solution of mixture of antimicrobial glycolipids in the cloudy beverage Orange Lemonade reasonable safe stabilization can be achieved by adding 50 µg/ml beta-cyclodextrin. As demonstrated in Example 7, the plain 25 µg/ml solution of a mixture of antimicrobial glycolipids in the cloudy beverage Orange Lemonade displayed precipitation already after 3 days.

Example 8: Application of Stock Solutions from Example 3 in Water Based Products 2×400 ml of two beverages, "Gerolsteiner Orangenlimonade" (orange lemonade, de-gassed, cloudy beverage) and "Kastell Zitronensprudel" (citrus lemonade, sterile filtered, clear beverage), each were fitted into a 500 mL Erlenmeyer flask. Subsequently, a defined volume, as shown in the table below, of the stock solution, as generated under Example 3, was poured into the beverages and stirred for 5 min, at room temperature:

| | Beverage | | | |
|---|---|---|---|---|
| | citrus lemonade | | orange lemonade | |
| | 6-1 PS80-1 | 6-2 PS80-2 | 6-3 PS80-1 | 6-4 PS80-2 |
| Stock solution (see Example 3) | 3-1 | 3-2 | 3-1 | 3-2 |
| v Beverage | 400 ml | 400 ml | 400 ml | 400 ml |
| v Stock solution | 0.5 ml | 0.5 ml | 1.25 ml | 1.25 ml |
| c Polysorbate 80 | 100 µg/ml | 100 µg/ml | 250 µg/ml | 250 µg/ml |
| c mixture antimicrobial glycolipids | 10 µg/ml | 25 µg/ml | 25 µg/ml | 100 µg/ml |

2×50 mL portion of the four solutions in the Erlenmeyer flasks were poured into clear and sterile polystyrol conical tubes and sealed for investigation of stability and compatibility of such beverages at three different temperatures (6/20/40° C.) each, resulting in four tubes per temperature and beverage. Such 24 tubes were stored for seven days and observed at day 0, 3 and 7 by measurement of turbidity as well as by optical inspection. A control solution without adding any components was run in parallel.

The results are depicted in the following tables; without additives means that neither stock solution, nor polysorbate 80 or a mixture of antimicrobial glycolipids was added.

a) Citrus Lemonade

Results of the turbidity measurements at 6° C., 20° C. and 40° C. are summarized in the tables below:

| | 6° C. Polysorbate 80 0.1 g/L | | | | |
|---|---|---|---|---|---|
| time [d] | control | 6-1 10 µg/ml | | 6-2 25 µg/ml | |
| 0 | 0.58 NTU | 0.56 NTU | 0.57 NTU | 0.61 NTU | 0.63 NTU |
| 3 | 0.63 NTU | 0.64 NTU | 0.62 NTU | 0.64 NTU | 0.68 NTU |
| 7 | 0.60 NTU | 0.62 NTU | 0.62 NTU | 0.64 NTU | 0.64 NTU |

| | | 20° C. Polysorbate 80 0.1 g/L | | | |
|---|---|---|---|---|---|
| time [d] | control | 6-1 10 µg/ml | | 6-2 25 µg/ml | |
| 0 | 0.57 NTU | 0.59 NTU | 0.53 NTU | 0.64 NTU | 0.65 NTU |
| 3 | 0.60 NTU | 0.59 NTU | 0.61 NTU | 0.54 NTU | 0.53 NTU |
| 7 | 0.58 NTU | 0.60 NTU | 0.60 NTU | 0.61 NTU | 0.61 NTU |

| | | 40° C. Polysorbate 80 0.1 g/L | | | |
|---|---|---|---|---|---|
| time [d] | control | 6-1 10 µg/ml | | 6-2 25 µg/ml | |
| 0 | 0.58 NTU | 0.59 NTU | 0.58 NTU | 0.64 NTU | 0.66 NTU |
| 3 | 0.58 NTU | 0.58 NTU | 0.58 NTU | 0.58 NTU | 0.59 NTU |
| 7 | 0.62 NTU | 0.63 NTU | 0.60 NTU | 0.64 NTU | 0.60 NTU |

Results of the visual control at 6° C., 20° C. and 40° C. are summarized in the tables below:

| | | 6° C. Polysorbate 80 0.1 g/L | | | |
|---|---|---|---|---|---|
| Time [d] | control | 6-1 10 µg/ml | | 6-2 25 µg/ml | |
| 0 | Clear solution, no particles, no precipitates | Same as control | Same as control | Same as control | Same as control |
| 3 | Clear solution, no particles, no precipitates | Same as control | Same as control | Same as control | Same as control |
| 7 | Clear solution, no particles, no precipitates | Same as control | Same as control | Same as control | Same as control |

| | | 20° C. Polysorbate 80 0.1 g/L | | | |
|---|---|---|---|---|---|
| Time [d] | control | 6-1 10 µg/ml | | 6-2 25 µg/ml | |
| 0 | Clear solution, no particles, no precipitates | Same as control | Same as control | Same as control | Same as control |
| 3 | Clear solution, no particles, no precipitates | Same as control | Same as control | Same as control | Same as control |
| 7 | Clear solution, no particles, no precipitates | Same as control | Same as control | Same as control | Same as control |

| | | 40° C. Polysorbate 80 0.1 g/L | | | |
|---|---|---|---|---|---|
| Time [d] | control | 6-1 10 µg/ml | | 6-2 25 µg/ml | |
| 0 | Clear solution, no particles, no precipitates | Same as control | Same as control | Same as control | Same as control |
| 3 | Clear solution, no particles, no precipitates | Same as control | Same as control | Same as control | Same as control |
| 7 | Clear solution, no particles, no precipitates | Same as control | Same as control | Same as control | Same as control | b) Orange Lemonade

Results of the turbidity measurements at 6° C., 20° C. and 40° C. are summarized in the tables below:

| | | 6° C. Polysorbate 80 0.25 g/L | | | |
|---|---|---|---|---|---|
| time [d] | Control* | 6-3 25 µg/ml | | 6-4 100 µg/ml | |
| 0 | 324 NTU | 280 NTU | 278 NTU | 221 NTU | 219 NTU |
| 3 | 293 NTU | 257 NTU | 261 NTU | 205 NTU | 204 NTU |
| 7 | 266 NTU | 245 NTU | 242 NTU | 201 NTU | 199 NTU |

| | | 20° C. Polysorbate 80 0.25 g/L | | | |
|---|---|---|---|---|---|
| time [d] | control | 6-3 25 µg/ml | | 6-4 100 µg/ml | |
| 0 | 324 NTU | 281 NTU | 274 NTU | 229 NTU | 221 NTU |
| 3 | 273 NTU | 223 NTU | 228 NTU | 183 NTU | 185 NTU |
| 7 | 260 NTU | 204 NTU | 204 NTU | 64 NTU | 66 NTU |

| | | 40° C. Polysorbate 80 0.25 g/L | | | |
|---|---|---|---|---|---|
| time [d] | control | 6-3 25 µg/ml | | 6-4 100 µg/ml | |
| 0 | 310 NTU | 280 NTU | 277 NTU | 226 NTU | 216 NTU |
| 3 | 254 NTU | 174 NTU | 175 NTU | 126 NTU | 101 NTU |
| 7 | 244 NTU | 163 NTU | 168 NTU | 95 NTU | 94 NTU |

Results of the visual control at 6° C., 20° C. and 40° C. are summarized in the tables below:

| | | 6° C. Polysorbate 80 0.25 g/L | | | |
|---|---|---|---|---|---|
| Time [d] | control | 6-3 25 µg/ml | | 6-4 100 µg/ml | |
| 0 | Clear solution, no particles, no precipitates | Same as control | Same as control | Same as control | Same as control |
| 3 | Clear solution, no particles, weak precipitation | Slightly turbid, no particles, weak precipitate | Slightly turbid, no particles, weak precipitate | Trub, keine Partikel, kein Bodensatz | Trub, keine Partikel, kein Bodensatz |
| 7 | Clear solution, no particles, weak precipitation | Same as control | Same as control | Same as control | Same as control |

| | 20° C. Polysorbate 80 0.25 g/L | | | |
|---|---|---|---|---|
| Time [d] | control | 6-3 25 µg/ml | | 6-4 100 µg/ml | |
| 0 | Clear solution, no particles, no precipitates | Same as control | Same as control | Same as control | Same as control |
| 3 | Clear solution, no particles, weak precipitation | Slightly turbid, no particles, weak precipitate | Slightly turbid, no particles, weak precipitate | Turbid, no particles, no precipitate | Turbid, no particles, no precipitate |
| 7 | Clear solution, no particles, weak precipitation | Same as control | Same as control | separation of liquid phases, particles | separation of liquid phases, particles |

| | 40° C. Polysorbate 80 0.25 g/L | | | |
|---|---|---|---|---|
| Time [d] | control | 6-3 25 µg/ml | | 6-4 100 µg/ml | |
| 0 | Clear solution, no particles, no precipitates | Same as control | Same as control | Same as control | Same as control |
| 3 | Clear solution, no particles, weak precipitation | Same as control | Same as control | Clear solution, particles, strong precipitation | Clear solution, particles, strong precipitation |
| 7 | Clear solution, no particles, weak precipitation | Same as control | Same as control | Clear solution, particles, strong precipitation | Clear solution, particles, strong precipitation |

*control means that neither polysorbate 80 nor a mixture of antimicrobial glycolipids was added It can be concluded from the above experimental data that the 10 µg/ml and 25 µg/ml solution of a mixture of antimicrobial glycolipids in the clear beverage Citrus Lemonade can safely be stabilized by combination with 100 µg/ml Polysorbate 80; this stability could be even confirmed for three different storage temperatures. As demonstrated in Example 7, the plain 10 µg/ml solution of a mixture of antimicrobial glycolipids in the clear beverage Citrus Lemonade displayed precipitation already after 3 days. For the 25 µg/ml solution of mixture of antimicrobial glycolipids in the cloudy beverage Orange Lemonade safe stabilisation can be achieved by adding 250 µg/ml Polysorbate 80 whereas the amount of 250 µg/ml Polysorbate 80 combined with 100 µg/ml of mixture of antimicrobial glycolipids obviously is not sufficient due to the observed increase precipitation and reduced turbidity after 7 days. As demonstrated in Example 7, the plain 25 µg/ml solution of a mixture of antimicrobial glycolipids in the cloudy beverage Orange Lemonade displayed precipitation already after 3 days.

Example 9: Compatibility Experiments of a Mixture of Antimicrobial Glycolipids without Applying any Formulation Stabilizer For comparison a mixture of antimicrobial glycolipids was applied to the beverages used in Examples 4-8 without applying any of the formulation stabilizers, i.e. polysorbates and cyclodextrins.

Portions of about 50 mL each for the three beverages, "Gerolsteiner Orangenlimonade" (orange lemonade, de-gassed, cloudy beverage), "Kastell Zitronensprudel" (citrus lemonade, sterile filtered, clear beverage), and "REWE Apfelsaft" (clear apple juice, sterile filtered, clear beverage), were mixed with aliquots of a mixture of antimicrobial glycolipids as to establish the nine test solutions; three control solutions without adding a mixture of antimicrobial glycolipids were ran in parallel:

| 7-1 | 7-2 | 7-3 | 7-4 |
|---|---|---|---|
| control | mixture of antimicrobial glycolipids 5 µg/ml | mixture of antimicrobial glycolipids 10 µg/ml | mixture of antimicrobial glycolipids 25 µg/ml |

Test sample preparation and experimental processing was identical as outlined in Examples 4 and 5 and visual observation revealed the following results:

"REWE Apfelsaft" (apple juice, sterile filtered):

| time [d] | 7-11 control | mixture of antimicrobial glycolipids [µg/ml] 7-21 5 µg/ml | 7-31 10 µg/ml | 7-41 25 µg/ml |
| --- | --- | --- | --- | --- |
| 0 | Clear, no particle, no precipitate | Same as control | Slight turbidity | Slight turbidity |
| 3 | Clear, no particle, no precipitate | Same as control | Clear but slight precipitation | Clear but strong precipitation |
| 7 | Clear, no particle, no precipitate | Same as control | Clear but slight precipitation | Clear but strong precipitation |
| 14 | Clear, no particle, no precipitate | Same as control | | |

"Gerolsteiner Orangenlimonade" (orange lemonade, degassed):

| time [d] | 7-12 control | mixture of antimicrobial glycolipids [µg/ml] 7-22 5 µg/ml | 7-32 10 µg/ml | 7-42 25 µg/ml |
| --- | --- | --- | --- | --- |
| 0 | Turbid, no particles, no precipitation | Same as control | Same as control | Less turbid |
| 3 | Turbid, no particles, no precipitation | Same as control | Same as control | Clear, precipitation |
| 7 | Turbid, no particles, no precipitation | Same as control | Same as control | Clear, precipitation |
| 14 | Turbid, no particles, no precipitation | Same as control | Same as control | — |

"Kastell Zitronensprudel" (citrus lemonade, sterile filtered):

| time [d] | 7-13 control | mixture of antimicrobial glycolipids [µg/ml] 7-23 5 µg/ml | 7-33 10 µg/ml | 7-43 25 µg/ml |
| --- | --- | --- | --- | --- |
| 0 | clear, no particles, no precipitation | Same as control | Same as control | Same as control |
| 3 | clear, no particles, no precipitation | Same as control | Slight precipitate | Slight precipitate |
| 7 | clear, no particles, no precipitation | Same as control | Same as control | precipitation |
| 14 | clear, no particles, no precipitation | Same as control | Same as control | — |

It can be concluded from the above experimental data that the compatibility of a mixture of antimicrobial glycolipids dissolved in the clear beverage Citrus Lemonade and Apple juice, as used here, is limited to a concentration of 10 µg/ml whereas at concentration of 25 µg/ml precipitation can be observed already after 3 becoming prominent after 7 days. Compatibility of a mixture of antimicrobial glycolipids dissolved in the cloudy beverage Orange Lemonade, as used here, is limited to an even lower concentration of 5 µg/ml whereas at a concentration of 10 µg/ml precipitation can be observed already after 3 days. In case stability is given after 7 days it stays stable even after 14 days.

Example 10: Comparison of Minimum Inhibitory Concentrations (MICs) of a Mixture Antimicrobial Glycolipids Alone or in Combination with Formulation Stabilisers The table below lists the MIC values determined for a mixture antimicrobial glycolipids alone or in combination with formulation stabilizers for two spoiling organisms: *Saccharomyces cerevisiae* MUCL 53497 and *Aspergillus niger* ATCC 16404:

| MIC [µg/mL] of glycolipids | | *S. cerevisiae* | | *A. niger* | |
|---|---|---|---|---|---|
| | | inventive in | | inventive in | |
| Formulation stabilizer | Concentration of formulation stabilizer [µg/mL] | combination with formulation stabilizer | comparative without formulation stabilizer | combination with formulation stabilizer | comparative without formulation stabilizer |
| alpha-Cyclodextrin | 25 | 25 | 12.5 | 12.5 | 3.1 |
| | 50 | 12.5 | 6.3 | 3.1 | 3.1 |
| | 100 | 25 | 12.5 | 3.1 | 3.1 |
| | 250 | 50 | 50 | 3.1 | 3.1 |
| | 500 | 100 | 50 | 12.5 | 3.1 |
| beta-Cyclodextrin | 100 | 12.5 | 6.3 | 3.1 | 3.1 |
| | 250 | 25 | 25 | 12.5 | 3.1 |
| | 500 | 25 | 12.5 | 3.1 | 3.1 |
| Methyl-beta-cyclodextrin | 50 | 12.5 | 6.3 | 3.1 | 3.1 |
| | 100 | 25 | 12.5 | 3.1 | 3.1 |
| | 250 | 50 | 25 | 3.1 | 3.1 |
| Hydroxypropyl-beta-cyclodextrin | 250 | 25 | 12.5 | 6.3 | 3.1 |
| | 1000 | 50 | 50 | 6.3 | 3.1 |
| | 100 | 12.5 | 3.1 | 6.3 | 1.6 |
| | 250 | 25 | 3.1 | 12.5 | 1.6 |
| Polysorbate 20 | 100 | 6.3 | 3.1 | 6.3 | 12.5 |
| | 250 | 25 | 3.1 | 12.5 | 12.5 |
| Polysorbate 60 | 75 | 12.5 | 3.1 | 6.3 | 12.5 |
| | 100 | 12.5 | 3.1 | 6.3 | 12.5 |
| Polysorbate 80 | 50 | 50 | 12.5 | 12.5 | 3.1 |
| | 100 | 12.5 | 6.3 | 3.1 | 1.6 |
| | 250 | 25 | 12.5 | 3.1 | 1.6 |
| | 500 | 100 | 25 | 12.5 | 3.1 |

Combinations were carried out using different concentrations of formulation stabilizers, as indicated. MIC values were determined by inoculation with 1×10E5 CFU/mL of the corresponding micro-organism, subsequent incubation in SDB medium at 28° C. for 48 h and visual inspection of microbial growth. The lowest concentration without detectable microbial growth was considered as MIC. All determinations were done in duplicate.

It can be concluded from the above experimental data that a mixture antimicrobial glycolipids retains its antimicrobial efficacy, as demonstrated above by the MIC values against the yeast and mold strain even in combination with cyclodextrins and polysorbates, as listed. However, the MIC value depends on the concentration of cyclodextrins and polysorbates used, i.e. the higher the concentrations of cyclodextrins and polysorbates are the higher the MIC values were measured. Beyond a concentration level of 500 µg/ml, cyclodextrins or polysorbates, the mixture antimicrobial glycolipids becomes ineffective.

Example 11: Application of Combinations of methyl-beta-cyclodextrin and a Mixture of Antimicrobial Glycolipids As to confirm the formulation stabilization properties of methyl-beta-cyclodextrin for the use of a mixture of antimicrobial glycolipids in water based products, in particular beverages, combinations of both components at different concentrations were investigated in two commercially available beverages which lack compatibility using a mixture of antimicrobial glycolipids alone, i.e. in the absence of methyl-beta-cyclodextrin.

Two beverages, "Gerolsteiner Orangenlimonade" (turbid orange lemonade, de-gassed; cloudy beverage) and "REWE Apfelsaft" (clear apple juice, sterile filtered; clear beverage), were used and test solutions prepared as described for Example 5 applying a stock solution of 50 mg/ml methyl-beta-cyclodextrin as well as a 5 mg/ml stock solution of a mixture of antimicrobial glycolipids both in sterile water, respectively.

For measurement of the turbidity the turbidity infrared device AL250T-IR from AQUALYTIC® was used. It was measured at five time points: day 0, 3, 7, 14 and 28. All test samples were stored and handled at room temperature.

Results on compatibility for Orange Lemonade and Apple Juice:

| Beverage | Apple Juice | | | | | |
|---|---|---|---|---|---|---|
| mixture of antimicrobial glycolipids [µg/mL] | 0 | 10 | 10 | 10 | 10 | 10 |
| methyl-beta-cyclodextrin [µg/mL] | 0 | 50 | 75 | 100 | 150 | 250 |
| methyl-beta-cyclodextrin vs. mixture of antimicrobial glycolipids | — | 5 | 7.5 | 10 | 15 | 25 |
| time [d] | turbidity [NTU] | | | | | |
| 0 | 0.67 | 1.71 | 1.21 | 1.05 | 0.92 | 0.88 |
| 28 | 0.72 | 0.86 | 1.50 | 1.77 | 1.78 | 1.80 |
| | Visual observation | | | | | |
| 0 | clear, no particles, not precipitate | weakly turbid, no particles, no precipitate | Same as control | Same as control | Same as control | Same as control |
| 7 | clear, no particles, not precipitate | weakly turbid, no particles, no precipitate | Same as control | Same as control | Same as control | Same as control |
| 14 | clear, no particles, not precipitate | weakly turbid, no panicles, no precipitate | Same as control | Same as control | Same as control | Same as control |
| 21 | clear, no particles, not precipitate | weakly turbid, no particles, no precipitate | Same as control | Same as control | Same as control | Same as control |
| 28 | clear, no particles, not precipitate | Small precipitate | Same as control | Same as control | Same as control | Same as control |

| Beveragae | Orange Lemonade | | | | | |
|---|---|---|---|---|---|---|
| mixture of antimicrobial glycolipids [µg/mL] | 0 | 25 | 25 | 25 | 25 | 25 |
| methyl-beta-cyclodextrin [µg/mL] | 0 | 100 | 250 | 375 | 500 | 1000 |
| methyl-beta-cyclodextrin vs. mixture of antimicrobial glycolipids | — | 4 | 10 | 15 | 20 | 40 |
| time [d] | turbidity [NTU] | | | | | |
| 0 | 274 | 283 | 270 | 269 | 258 | 244 |
| 28 | 194 | 145 | 161 | 173 | 189 | 185 |
| | Visual observation | | | | | |
| 0 | Turbid, no particles, no precipitate | Same as control | Same as control | Same as control | Same as control | Same as control |
| 7 | Turbid, no particles, no precipitate | precipitate | Same as control | Same as control | Same as control | Same as control |
| 14 | Turbid, no particles, no precipitate | precipitate | Cloudy, small precipitate | Small precipitate | Same as control | Same as control |
| 21 | Turbid, no particles, no precipitate | precipitate | Cloudy, small precipitate | Small precipitate | Same as control | Same as control |
| 28 | Turbid, no particles, no precipitate | precipitate | Cloudy, small precipitate | Small precipitate | Same as control | Same as control |

It can be concluded from the above experimental data that the 10 µg/ml solution of a mixture of antimicrobial glycolipids in the clear beverage Apple Juice can safely be stabilized for 28 d by combining with 75 µg/ml methyl-beta-cyclodextrin whereas amounts of 50 µg/ml methyl-beta-cyclodextrin obviously are not yet sufficient due to the observed small precipitation. As demonstrated in Example 9, the plain 10 µg/ml solution of a mixture of antimicrobial glycolipids in the clear beverage Apple Juice displayed precipitation already after 3 days. For the 25 µg/ml solution of mixture of antimicrobial glycolipids in the cloudy beverage Orange Lemonade safe stabilization can be achieved for 28 d by adding 500 µg/ml methyl-beta-cyclodextrin whereas amounts of 250 µg/ml methyl-beta-cyclodextrin obviously are not yet sufficient due to the observed increase in turbidity and precipitation after 14 days. As demonstrated in Example 9, the plain 25 µg/ml solution of a mixture of antimicrobial glycolipids in the cloudy beverage Orange Lemonade displayed precipitation already after 3 days.

Example 12: Application of Combinations of hydroxypropyl-beta-cyclodextrin and a Mixture of Antimicrobial Glycolipids As to confirm the compatibility improving properties of hydroxypropyl-beta-cyclodextrin for the use of a mixture of antimicrobial glycolipids in water based products, in particular beverages, combinations of both components at different concentrations were investigated in two commercially available beverages which lack compatibility using a mixture of antimicrobial glycolipids alone, i.e. in the absence of hydroxypropyl-beta-cyclodextrin.

Two beverages, "Gerolsteiner Orangenlimonade" (turbid orange lemonade, de-gassed; cloudy beverage) and "REWE Apfelsaft" (clear apple juice, sterile filtered; clear beverage), were used and test solutions prepared as described for Example 5 applying a stock solution of 5 µg/ml hydroxypropyl-beta-cyclodextrin as well as a 5 µg/ml stock solution of a mixture of antimicrobial glycolipids both in sterile water, respectively.

For measurement of the turbidity the turbidity infrared device AL250T-IR from AQUALYTIC® was used. It was measured at five time points: day 0, 3, 7, 14 and 28. All test samples were stored and handled at room temperature.

Results on compatibility for Orange Lemonade and Apple Juice:

| Beverage | Apple Juice | | | | | |
|---|---|---|---|---|---|---|
| mixture of antimicrobial glycolipids [µg/mL] | 0 | 10 | 10 | 10 | 10 | 10 |
| hydroxypropyl-beta-cyclodextrin [µg/mL] | 0 | 50 | 75 | 100 | 150 | 250 |
| hydroxypropyl-beta-cyclodextrin vs. mixture of antimicrobial glycolipids | — | 5 | 7.5 | 10 | 15 | 25 |
| time [d] | turbidity [NTU] | | | | | |
| 0 | 0.68 | 2.03 | 1.55 | 1.86 | 1.49 | 1.09 |
| 28 | 0.75 | 0.76 | 0.8 | 0.81 | 0.93 | 1.86 |
| | Visual observation | | | | | |
| 0 | clear, no particles, not precipitate | Weakly turbid, no particles, not precipitate | Weakly turbid, no particles, not precipitate | Weakly turbid, no particles, not precipitate | Same as control | Same as control |
| 7 | clear, no particles, not precipitate | particles | Small particles | Thin particles | Same as control | Same as control |
| 14 | clear, no particles, not precipitate | particles | Small particles | Thin particles | Same as control | Same as control |
| 21 | clear, no particles, not precipitate | particles | Small particles | This particles | Same as control | Same as control |
| 28 | clear, no particles, not precipitate | particles | Small particles | Thin particles | Same as control | Same as control |

| Beverage | Orange Lemonade | | | | | |
|---|---|---|---|---|---|---|
| mixture of antimicrobial glycolipids [µg/mL] | 0 | 25 | 25 | 25 | 25 | 25 |
| hydroxypropyl-beta-cyclodextrin [µg/mL] | 0 | 100 | 250 | 375 | 500 | 1000 |
| hydroxypropyl-beta-cyclodextrin vs. mixture of antimicrobial glycolipids | — | 4 | 10 | 15 | 20 | 40 |
| time [d] | turbidity [NTU] | | | | | |
| 0 | 276 | 272 | 272 | 257 | 261 | 249 |
| 28 | 197 | 148 | 148 | 152 | 158 | 176 |
| | Visual observation | | | | | |
| 0 | Turbid, no particles, no precipitate | Same as control | Same as control | Same as control | Same as control | Same as control |
| 7 | Turbid, no particles, no precipitate | precipitate | precipitate | precipitate | Small precipitate | Same as control |
| 14 | Turbid, no particles, no precipitate | precipitate | precipitate | precipitate | Small precipitate | Same as control |
| 21 | Turbid, no particles, no precipitate | precipitate | precipitate | precipitate | Small precipitate | Same as control |
| 28 | Turbid, no particles, no precipitate | precipitate | precipitate | precipitate | Small precipitate | Very little precipitation |

It can be concluded from the above experimental data that the 10 µg/ml solution of a mixture of antimicrobial glycolipids in the clear beverage Apple Juice can safely be stabilized for 28 d by combining with 150 µg/ml hydroxypropyl-beta-cyclodextrin whereas amounts of 100 µg/ml hydroxypropyl-beta-cyclodextrin obviously are not yet sufficient due to the observed small precipitation. As demonstrated in Example 9, the plain 10 µg/ml solution of a mixture of antimicrobial glycolipids in the clear beverage Apple Juice displayed precipitation already after 3 days. For the 25 µg/ml solution of mixture of antimicrobial glycolipids in the cloudy beverage Orange Lemonade safe stabilization can be achieved for 28 d by adding 1000 µg/ml hydroxypropyl-beta-cyclodextrin whereas amounts of 500 µg/ml hydroxypropyl-beta-cyclodextrin obviously are not yet sufficient due to the observed increase in turbidity and precipitation after 7 days. As demonstrated in Example 9, the plain 25 µg/ml solution of a mixture of antimicrobial glycolipids in the cloudy beverage Orange Lemonade displayed precipitation already after 3 days.

Example 13: Preserving Challenge Tests of a Mixture of Antimicrobial Glycolipids in Combination with Formulation Stabiliser in Selected Beverages Case 1: Volvic Juicy Sommerfrüchte (Fruit Drink 10% Juice)

a) Initial experiments showed that addition of a mixture of antimicrobial glycolipids according w the invention (in the following also abbreviated as "AGL") into this fruit drink leads to slight incompatibilities regarding the visual appearance of the beverage.

| | c (AGL) [µg/ml] | | | |
|---|---|---|---|---|
| Time: | 0 (control) | 5 | 10 | 25 |
| | Visual appearance | | | |
| 1 h | weakly turbid, no particles, no sediment | same as control | same as control | same as control |
| 28 d | clear, no particles, thin sediment | similar as control, slightly more sediment | similar as control, more sediment | cloudy particles, predominantly at the at the bottom |
| | Turbidity [NTU] | | | |
| 1 h | 6.11 | 7.68 | 8.70 | 11.40 |
| 28 d | 0.60 | 0.57 | 0.49 | 0.49 |

The observed incompatibility effects were further increased when the experiment was repeated at 6° C. (i.e. refrigerator conditions).

b) However, when the fruit drink containing 5 or 10 µg/ml AGL was challenged by adding certain food-spoiling microorganisms, it was shown that the tested AGL concentrations safely prevent spoilage of the beverage. No viable microorganisms were found in the beverage compositions after 28 day inoculation period at room temperature.

The preserving challenge test was carried out as follows:
The beverage was spoiled with a mixture of three yeasts or three molds. Yeast mixture: *Saccharomyces cerevisiae, Zygosacchammyces rouxii, Zygosacchoromyces bailii*. Mold mixture: *Aspergillus niger, Byssachlamys nivea, Pencillium roqueforti*. The mixture of glycolipids was added to the beverage in different concentrations, and afterward it was inoculated with either the yeast or the mold mixture with a concentration of 100 colony forming units (cfu) per ml for either of the mixtures. Incubation was done for 28 h days at room temperature, using sterile centrifuge tubes (50 ml) closed with a screw lid and filled with 40 ml beverage as vessel. The tubes were inspected visually on regular basis in order to assess physical compatibility as well as microbial growth. After 28 days, microbial growth was quantified by colony count on agar plates incubated for 72 h with 100 ml of each beverage sample.

c) In order to overcome the limited compatibility of AGL in this fruit drink, certain amounts of alpha-cyclodextrin (a-CD) as formulation stabilizer were added as to achieve a formulation exhibiting both physicochemical and antimicrobial stability.

Test parameters are given in the table below. The test for compatibility was combined with a preserving challenge test as described in the preceding paragraph (section b).

| c (α-CD) [μg/ml] | 0 (control) | 35 | 70 | 100 |
|---|---|---|---|---|
| c (AGL) [μg/ml] |  | 7 | 7 | 10 |
| Time: | Visual appearance | | | |
| 1 h | weakly turbid, no particles, no sediment | Same as control | Same as control | Same as con trol |
| 28 d | Clear, no particles, thin sediment | Same as control | Same as control | Same as control |

While the non-preserved control was completely spoiled with yeasts and molds after seven days at room temperature, no microbial spoilage was found in the formulations containing AGL and a-CD during the complete test period of 28 days. Colony count confirmed that no microbial growth occurred in these preparations.

Compatibility (i.e. absence of any visual differences between formulations containing AGL and the original beverage without AGL) was confirmed under refrigerator conditions (6° C.) for 28 days. No visual difference to control was observed.

Thus, the combination of AGL with a-CD as formulation stabilizer allows a safe preservation of the beverage against microbial spoilage.

Case 2: Schweppes Indian Tonic Water (Carbonated Soft Drink)

a) Initial experiments showed that addition of AGL into this carbonated soft drink leads to slight incompatibilities regarding the visual appearance of the beverage. In particular, the turbidity of the beverage increases slightly with the AGL concentration.

| | c (AGL) [μg/ml] | | | |
|---|---|---|---|---|
| Time: | 0 (control) | 5 | 10 | 25 |
| | Visual appearance | | | |
| 1 h | clear, no particles, no sediment | slightly turbid, no particles, no sediment | slightly turbid, no particles, no sediment | slightly turbid, no particles, no sediment |
| 28 d | clear, no particles, no sediment | slightly turbid, no particles, no sediment | similar as control, more sediment | cloudy particles, predominantly at the at the bottom |
| | Turbidity [NTU] | | | |
| 1 h | 0.66 | 1.89 | 3.06 | 5.94 |
| 28 d | 0.55 | 0.49 | 0.47 | 0.48 |

At refrigerator conditions (6° C.), compatibility was found to be worse due to particle formation.

b) A preserving challenge test (same method and conditions as for Case 1: Volvic Juicy Sommerfrüchte) showed that all tested AGL concentrations (5, 10, 25 μg/ml) safely prevented spoilage of the beverage. Despite the visual appearance changed as described in section a), no microbial growth occurred. Without addition of AGL, spoilage of the soft drink occurred after incubation for 14 d at room temperature.

c) Addition of a-CD as formulation stabilizer stabilized the beverage formulation and maintained the antimicrobial activity of the AGL. This was confirmed by repeating the preserving challenge test using concentrations as listed in the following table.

| c (α-CD) [μg/ml] | 0 (control) | 35 | 70 | 50 | 100 |
|---|---|---|---|---|---|
| c (AGL) [μg/ml] | | 7 | 7 | 10 | 10 |
| Time: | Visual appearance | | | | |
| 1 h | clear, no particles, no sediment | Same as control | Same as control | Same as control | Same as control |
| 28 d | clear, no paricles, no sediment | Same as control | Same as control | Same as control | Same as control |

While the non-preserved control was spoiled with yeasts and molds after 14 days at room temperature, no microbial growth was found in the formulations containing AGL and a-CD during the complete test period of 28 days. Colony count confirmed that no microbial growth had occurred in these preparations.

Compatibility (i.e. absence of any visual differences between formulations containing AGL and the original beverage without AGL) was confirmed under refrigerator conditions (6° C.) for 28 days. No visual difference to control was observed.

Thus, the combination of AGL with a-CD as formulation stabilizer allows a safe preservation of the beverage against microbial spoilage.

Case 3: Clear Apple Juice a,b) Initial experiments showed that addition of 5 µg/ml AGL (or higher concentrations) into clear apple juice safely protected against microbial growth in a challenge test as described before (Case 1, section b). However, addition of AGL to apple juice also provoked formation of thin sediment (at 5 µg/ml AGL) or cloudy particles (at 5 and 10 µg/ml AGL).

c) Addition of a-CD as formulation stabilizer stabilized the beverage formulation and maintained the antimicrobial activity of AGL. This was confirmed by repeating the preserving challenge test using concentrations as listed in the following table.

| c (α-CD) [µg/ml] | 0 (control) | 70 | 100 |
|---|---|---|---|
| c (AGL) [µg/ml] | | 7 | 10 |
| Time: | Visual appearance | | |
| 1 h | clear, no particles, no sediment | Same as control | Same as control |
| 28 d | clear, no particles, very thin sediment | Same as control | Same as control |

While the non-preserved control was spoiled with yeasts and molds after 2 days at room temperature, no microbial growth was found in the formulations containing AGL and a-CD during the test period of 28 days. Colony count confirmed that no microbial growth had occurred in the preparations.

Compatibility (i.e. absence of any visual differences between formulations containing AGL and the original beverage without AGL) was also con finned under refrigerator conditions (6° C.) for 28 days. No visual difference to control was obtained.

Thus, the combination of AGL with a-CD as formulation stabilizer formulation stabilizer allows a safe preservation of the beverage against microbial spoilage.

Comparison of alpha-cyclodextrin with Polysorbate 60:

The preferred formulation stabilizers polysorbates and cyclodextrins have been further investigated towards their practicability in application in beverages as well as their reliability in use. The results are compiled its the following table:

| formulation stabilizer | handling | solubility in water | formulation stabilizing effect* | compatibility with water based products** |
|---|---|---|---|---|
| alpha-cyclodextrin | Powder, easy to weigh and dose | Very well soluble in water at ambient temperature | +++ | Very good, no negative interaction observed among 148 different beverages tested |
| polysorbate 60 | Thick liquid, quite demanding to precisely weigh and dose | Dissolution requires strong stirring and heating >50° C. | +++ | Not reliable: turbidity and precipitation observed for certain beverages |

*indicates the effect when applied to stabilize mixtures of antimicrobial glycolipids in a beverage, provided that the formulation stabilizer is compatible with the beverage when applied w/o mixtures of antimicrobial glycolipids
**indicates whether the formulation stabilizer is compatible when applied to the beverage w/o mixtures of antimicrobial glycolipids Although polysorbates demonstrate a good formulation stabilizing effect of water bases products when preserved with Glycolipids, polysorbates do have certain disadvantages in handling and solubility. In addition the reliability to be used in beverages is limited due to the observed limitation in compatibility. Therefore, the cyclodextrins, in particular alpha-cyclodextrin, appear superior as a broadly applicable and reliable formulation stabilizer for preservation of water based products with mixtures of antimicrobial glycolipids.

What is claimed is:

1. An orally consumable water based product comprising:
   (i) a glycolipid component comprising:
   at least one antimicrobial glycolipid according to general formula (I)

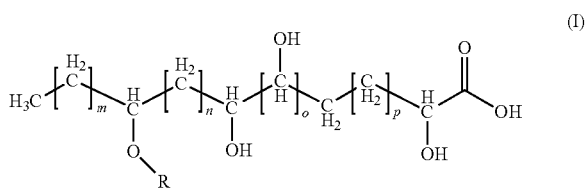

wherein
   m is 3 to 5;
   n is 2 to 5;
   o is 0 or 1; and
   p is 3 to 17;
   with the proviso that the sum m+n+o+p is not less than 14; and
   R is a carbohydrate moiety bound via one of its carbon atoms to the binding oxygen; and/or
   a physiologically acceptable salt thereof; and/or
   an ester thereof:
   in open chain form, wherein any of the hydroxyl groups of general formula (I) including any of the hydroxyl groups of the carbohydrate moiety R is intermolecularly esterified with a carboxylic acid; and/or
   in form of a lactone intramolecularly formed between the terminal carboxylic acid group of general formula (I) with any of the hydroxyl groups of general formula (I) including any of the hydroxyl groups of the carbohydrate moiety R; and
   (ii) a formulation component comprising at least cyclodextrins and/or polysorbates; and
   wherein the content of the glycolipid is within the range from 3 to 50 ppmw based on the total weight of the orally consumable water based product and the weight ratio of the formulation component to the glycolipid component is 10:1 to 2.5:1.

2. The orally consumable water based product according to claim 1, wherein the at least one antimicrobial glycolipid according to general formula (I) is an ester in open chain form, wherein the carboxylic acid is a $C_3$-$C_{10}$-alkanoic acid.

3. The orally consumable water based product according to claim 1, wherein the cyclodextrin is selected from alpha-cyclodextrin, beta-cyclodextrin, hydroxypropyl-beta-cyclodextrin and methyl-beta-cyclodextrin.

4. The composition according to claim 3, wherein the relative weight ratio of the cyclodextrin to the glycolipid component is 5:1 to 2.5:1.

5. The orally consumable water based product according to claim 1, wherein the polysorbate is selected from the group consisting of polysorbate 20, polysorbate 21, polysorbate 40, polysorbate 60, polysorbate 61, polysorbate 65, polysorbate 80, polysorbate 81, polysorbate 85, polysorbate 120, and a mixture of any of the foregoing.

6. The orally consumable water based product according to claim 1, wherein R is a moiety of the subformula

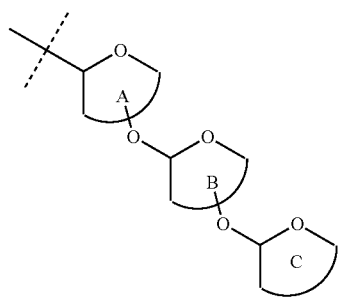

wherein the rings A, B and C are monosaccharide moieties, each independently from the others, with 5 or 6 ring members, wherein one or more of the hydroxyl groups may be acylated.

7. The orally consumable water based product according to claim 5, wherein the rings A and B are xylopyranose moieties and the ring C is a glucopyranose moiety.

8. The orally consumable water based product according to claim 1, wherein the at least one antimicrobial glycolipid is a glycolipid according to general formula (II)

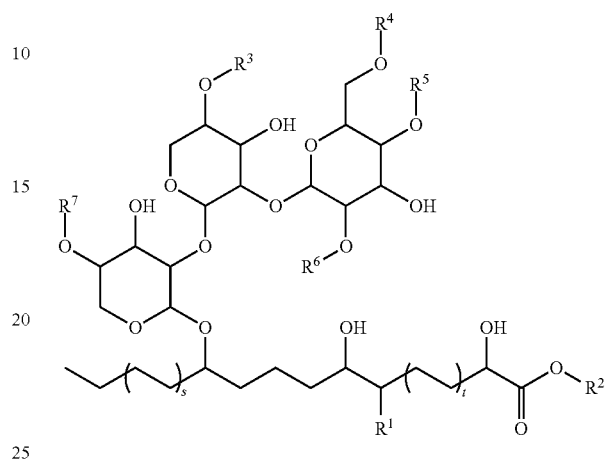

wherein
s is 1 or 2;
t is 6 or 7;
$R^1$ means —H or —OH;
$R^2$ means —H or —$C_1$-$C_6$-alkyl; and
$R^3$, $R^4$, $R^5$, $R^6$ and $R^7$, independently of one another, mean —H or —C(=O)$C_1$-$C_6$-alkyl.

9. The orally consumable water based product according to claim 7, wherein at least one of $R^3$, $R^4$, $R^5$, $R^6$ and $R^7$ means —C(=O)$C_1$-$C_6$-alkyl.

10. The orally consumable water based product according to claim 1, wherein the at least one antimicrobial glycolipid is selected from compounds (II-A) to (II-D),

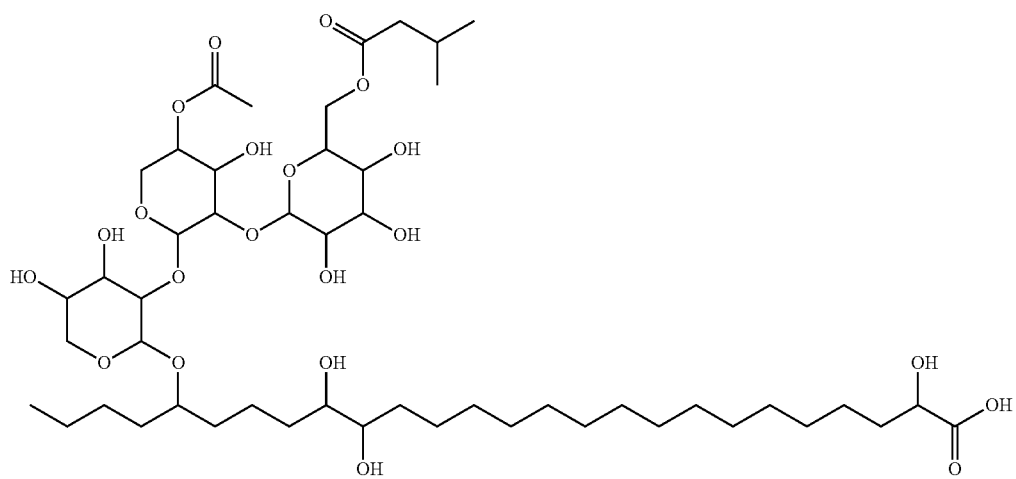

(II-B)
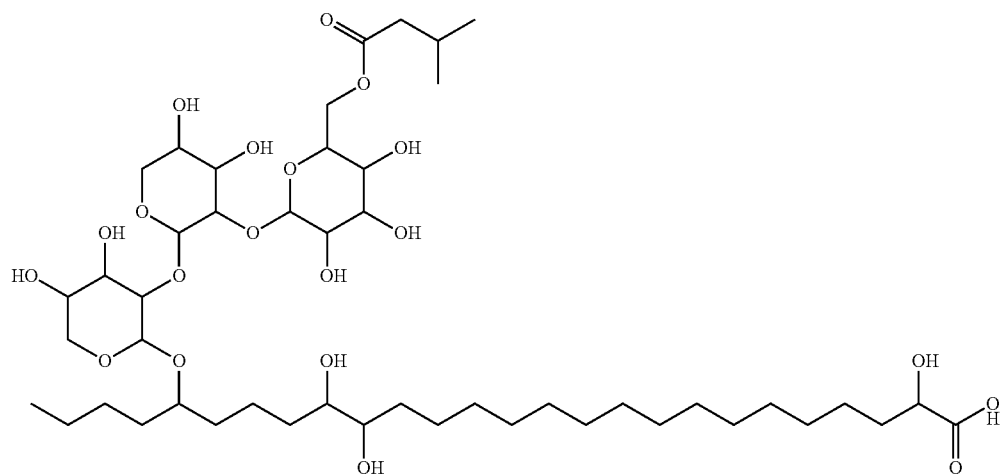
(II-C)
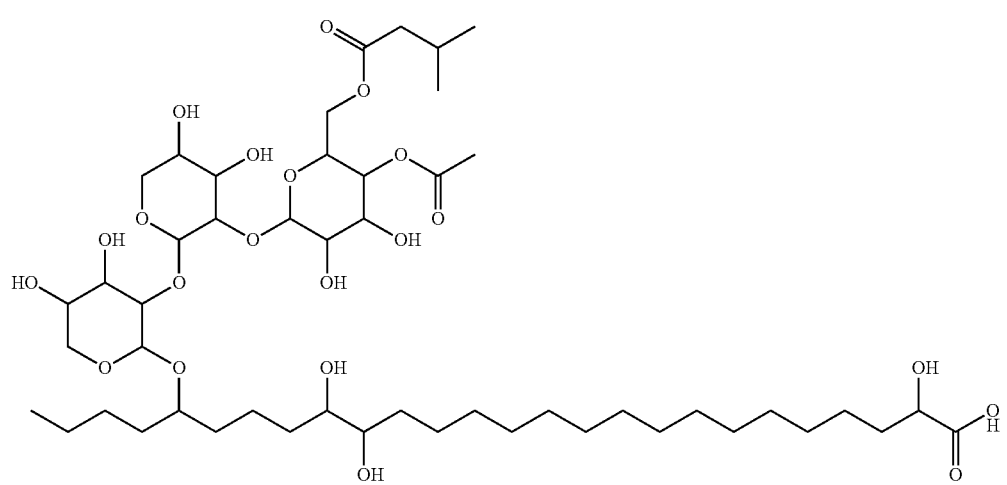
(II-D)
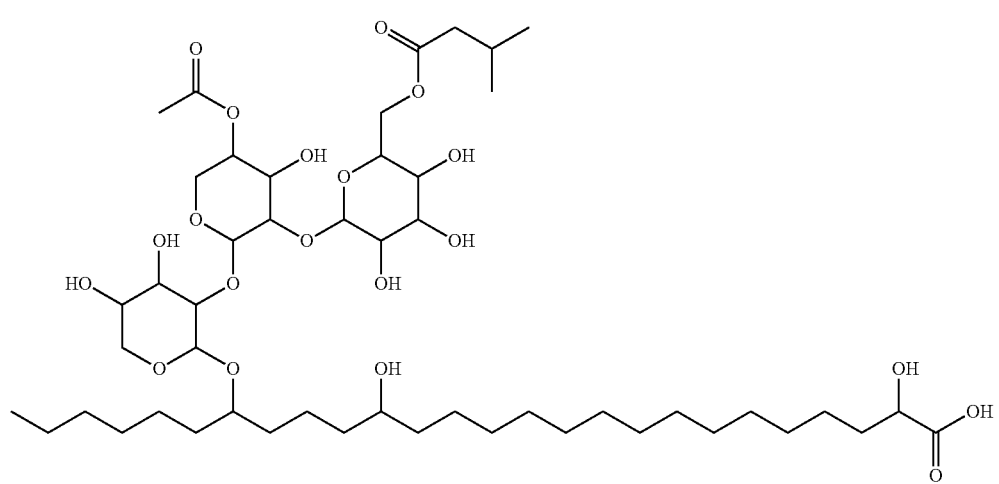

physiologically acceptable salts thereof, and mixtures thereof.

11. The orally consumable water based product according to claim 9, wherein the at least one antimicrobial glycolipid is compound (II-A) or a physiologically acceptable salts thereof.

12. The orally consumable water based product according to claim 1, wherein the glycolipid component comprises a mixture of more than one antimicrobial glycolipid according to general formula (I).

13. The orally consumable water based product according to claim 9, wherein the glycolipid component comprises a mixture of more than one antimicrobial glycolipid according to general formula (II).

14. The orally consumable water based product according to claim 12, wherein the glycolipid component comprises a mixture of at least a first, a second, and a third antimicrobial glycolipid according to general formula (II), wherein:
the relative weight content of the first antimicrobial glycolipid according to general formula (II) is 30 to 50 wt.-%;
the relative weight content of the second antimicrobial glycolipid according to general formula (II) is 20 to 50 wt.-%;
the relative weight content of the third antimicrobial glycolipid according to general formula (II) is 5 to 10 wt.-%,
relative to the total weight of all antimicrobial glycolipids that are comprised in the glycolipid component.

15. The orally consumable water based product according to claim 12, wherein the glycolipid component comprises a mixture of at least a first, a second, and a third antimicrobial glycolipid according to general formula (II), wherein:
the first antimicrobial glycolipid has a nominal molecular weight of ~970 Da;
the second antimicrobial glycolipid has a nominal molecular weight of ~1012 Da; and
the third antimicrobial glycolipid has a nominal molecular weight of ~1054 Da.

16. The orally consumable water based product according to claim 1, wherein the polysorbate is polysorbate 60.

* * * * *